United States Patent [19]

Wachter et al.

[11] Patent Number: 5,164,381

[45] Date of Patent: Nov. 17, 1992

[54] PHARMACOLOGICALLY ACTIVE 1,5-DIARYL-3-SUBSTITUTED PYRAZOLES AND METHOD FOR SYNTHESIZING THE SAME

[75] Inventors: Michael P. Wachter, Bloomsbury; Michael P. Ferro, Somerville, both of N.J.

[73] Assignee: Ortho Pharmaceutical Corporation, Raritan, N.J.

[21] Appl. No.: 730,515

[22] Filed: Jul. 12, 1991

Related U.S. Application Data

[63] Continuation of Ser. No. 339,272, Apr. 14, 1989, abandoned, which is a continuation-in-part of Ser. No. 42,661, Apr. 29, 1987, Pat. No. 4,826,868, which is a continuation of Ser. No. 867,996, May 29, 1986, abandoned.

[51] Int. Cl.$^5$ .................. C07D 231/10; A61K 31/38; A61K 31/415; A61K 31/425
[52] U.S. Cl. .......................... 514/85; 514/89; 514/93; 514/94; 514/236.5; 514/333; 514/341; 514/365; 514/369; 514/370; 514/381; 514/382; 514/406; 514/407; 514/90; 548/376.1; 548/375.1
[58] Field of Search ............ 548/378; 514/236.5, 514/255, 341, 370, 381, 406, 407, 85, 89, 94, 93, 333, 382, 365, 369, 90

[56] References Cited

PUBLICATIONS

Fulmer et al., J. Het. Chem., 17:799–800 (1980).
do Foote et al., J. Het. Chem., 7:89092 (1970).
Beam et al., J. Het. Chem., 9:183–185 (1972).
Soliman et al., J. Pharm. Sci., 70:602–610 (1981).
Barluenga et al., J.C.S. Chem. Comm., 891 (1979).
Virmani et al., Indian J. Chem., Sect. B, 17B:472–477 (1979).
Vereshchagin et al., Zh. Org. Khim., 7:907–912 (1971).
Jahn and Wagner–Jauregg, Arzneim-Forsch. (drug Res.), 24:494–499 (1974).
Shawali, J. Het. Chem., 14:375–81 (1977).
Shawali et al., J. Het. Chem., 13:989–92 (1976).
Matsumoto et al., Bull. Chem. Soc. Japan, 47:946–949 (1979).
Shrof et al., J. Med. Chem. 24:1521–1525 (1981).
El-Sayed and Ohta, Bull. Chem. Soc., Japan, 46:1801–1803 (1973).
Al-Saleh et al., J.C.S. Perkin I, 642–645 (1981).
Fusco and Croce, Gazz. Chim. Ital., 101:703–272 (1971).
Biere et al., Arch. Phar., 316:608–616 (1983).

Primary Examiner—Johann Richter

[57] ABSTRACT

1,5-Diaryl-3-substituted pyrazoles, a method of their preparation, compositions containing the same and methods of their use are disclosed. The pyrazoles are useful in alleviating inflammatory and cardiovascular disorders in mammals.

10 Claims, 1 Drawing Sheet

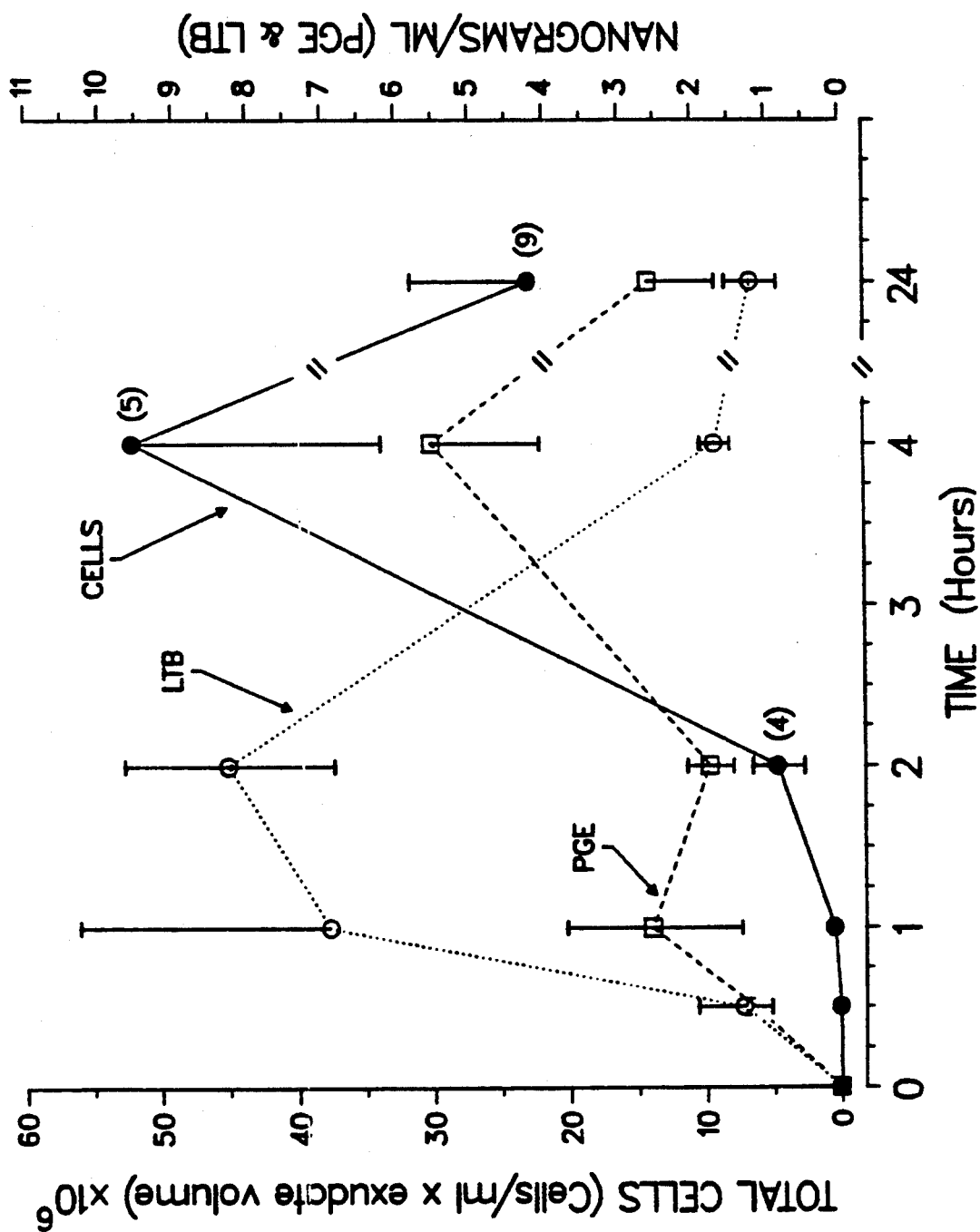

PHARMACOLOGICALLY ACTIVE 1,5-DIARYL-3-SUBSTITUTED PYRAZOLES AND METHOD FOR SYNTHESIZING THE SAME

This is a continuation of application Ser. No. 07/339,272, filed Apr. 14, 1989, now abandoned which is a continuation-in-part of application Ser. No. 042,661, filed Apr. 29, 1987 now U.S. Pat. No. 4,826,868, which in turn is a continuation of application Ser. No. 867,996, filed May 29, 1986 now abandoned.

DESCRIPTION

1. Technical Field

The present invention relates to substituted pyrazole derivatives, and particularly to 1,5-diaryl 3-substituted-pyrazoles that are pharmacologically active in alleviating inflammation, asthma, hypersensitivity, myocardial ischemia, dermatological conditions such as psoriasis, dermatitis and gastrointestinal inflammatory conditions such as inflammatory bowel syndromes, and to a method for synthesizing those pyrazole derivatives. The compounds of this invention may also be employed to treat or suppress the signs and symptoms of adult respiratory distress syndrome.

2. Background

Nonsteroidal anti-inflammatory drugs (NSAID's) such as indomethacin, naproxen, ibuprofen, tolectin, fenoprofen and the like have generally been shown to attenuate the biosynthesis of prostaglandins by inhibiting the activity of the enzyme cyclooxygenase. The prostaglandin end-products of the cyclooxygenase pathway are responsible for many of the early signs of inflammation including hyperalgesia, increases in vascular permeability leading to edema, and pyrexia. The activity and potency of the NSAID's in reducing these signs and symptoms is, for the most part, correlated with their ability to inhibit prostaglandin biosynthesis, and usually does not lead to permanent amelioration of inflammation.

The other major pathway of arachidonic acid metabolism is the lipoxygenase pathway. Lipoxygenase products of arachidonate metabolism, the leukotrienes, hydroxyeicosatetraenoic acids (HETES) and hydroperoxyeicosatetraenoic acids (HEPTES), have been shown or implicated to be involved in disease states including acute and chronic inflammation, arthritis, allergic and other hypersensitivity disorders, dermatological diseases such as psoriasis, acne, atopic dermatitis, contact sensitivity, eczema and others, cardiovascular disorders secondary to myocardial ischemia or infarction, thromboembolism or vasculitis or platelet aggregation, and hyperalgesic disorders, gynecological disorders such as dysmenorrhea, ocular inflammation, sperm motility or function, and others.

Leukotriene $B_4$ ($LTB_4$), another product of the lipoxygenase pathway, as well as HETES and HPETES can mediate induction of other phlogistic substances such as thromboxanes and prostacyclin, is chemotactic to inflammatory cells, and is hyperalgesic. Many of these mediators have been identified in skin, lungs, coronary circulation, eyes, gastrointestinal tract and other organs, and in the synovial fluid of rheumatoid arthritic patients. In chronic inflammatory conditions such as rheumatoid arthritis, it is believed to be the chronic influx of leukocytes, probably mediated by $LTB_4$, that is the eventual cause of joint erosion.

It is believed that inhibitors of the lipoxygenase pathway, as opposed to just cyclooxygenase inhibitors, could lead to a relatively permanent effect on inflammatory disorders such as rheumatoid arthritis since they could modulate the actual mechanisms of tissue and joint breakdown. Similarly, drugs that could inhibit prostaglandin synthesis via the cyclooxgenase pathway could modulate and reduce early manifestations of inflammation. Pharmacologically active compounds that can inhibit both enzyme pathways at similar concentrations (dual inhibitors) provide a more complete relief for patients suffering from arthritis, hypersensitivity, dermatological, cardiovascular, gastrointestinal, ocular, and gynecological disorders than present drugs that inhibit one pathway, but not the other as is the case for usually used NSAID's that are predominantly inhibitors of the cyclooxygenase (prostaglandin synthesis) pathway.

Leukotrienes (LTs), the products of 5-lipoxygenase-catalyzed oxygenation of arachidonic acid, appear to participate in a variety of acute and chronic inflammatory diseases. Leukotriene $B_4$ ($LTB_4$) is a potent stimulus for neutrophil activation, inducing neutrophil chemotaxis, aggregation and degradative enzyme release. These activities constitute the cellular component of inflammation and contribute to the development of chronic inflammation. Currently available anti-inflammatory drugs (non-steroidal anti-inflammatory drugs; NSAID's), are only able to inhibit the cyclooxygenase enzyme which metabolizes arachidonic acid to form prostaglandins. These molecules mediate the pain and edema (vascular changes) associated with inflammation which are controlled by NSAID's. However, the cellular infiltration of leukocytes associated with the destruction of tissues and the chronicity of inflammation is not suppressed by NSAID's. Therefore, drugs which inhibit both lipoxygenase and cyclooxygenase represent a new class of drugs which should be more effective in controlling inflammatory diseases.

$LTB_4$ has been found in inflammatory exudates or tissues from experimental animals and human diseases including synovial fluids from patients with rheumatoid arthritis and gout, ulcerative colitis and Crohn's disease, psoriasis, and chronic obstructive pulmonary diseases. In addition to the pro-inflammatory activities of $LTB_4$ and other lipoxygenase metabolites, these products have the ability to regulate immune reactions. Leukotrienes augment the cellular production of cytokines or interleukins which are potent molecular signals that activate or alter the behavior or function of a wide variety of immune or non-immune cells. Cytokines such as interleukin-1, interleukin-6, interleukin-2 and gamma-interferon are present in the synovial fluid of rheumatoid arthritis patients. They are believed to play a role in marshalling the intrasynovial immune response by activating effector lymphocytes, macrophages and granulocytes, which produce enzymes and mediators that contribute to the pannus formation and joint destruction in rheumatoid arthritis. Experimental and clinical evidence demonstrate the potential importance of interleukin-1 (IL-1) in orchestrating the immunopathology of rheumatoid arthritis. IL-1 has a role in the interactions between cells of the immune system and effector processes within joints. IL-1 activates T lymphocytes, which proliferate, elaborating cytokines which effect macrophage activities and antibody production by B-lymphocytes. IL-1 is also a potent bone resorbing factor via the activation of osteoclasts and osteoblasts. Chondrocytes and synovial fibroblasts produce collagenase, protoglycanase and prostaglandins when stimulated by IL-1 which mediate connective tissue destruction in arthritis.

Because lipoxygenase products are involved in augmenting cytokine production and are involved in the signal transduction of these molecules as they participate in the regulation of immune responses, inhibitors of the lipoxygenase enzyme would be expected to have a disease modifying activity in chronic immunoinflammatory diseases. Dinarello et al. [J. Immunol., 130, 890 (1983) and Int. J. Immunopharm., 6, 43 (1984)] have demonstrated that inhibitors of leukotriene synthesis block both IL-1 production and some of its biological activities. It has been reported that a dual cyclooxygenase/lipoxygenase inhibitor (CP 66,248) could inhibit interleukin-1 levels in vitro and in vivo [Arthritis Rheum., 31, S90, S89, S17 (1988)]. The reduction of IL-1 in the synovial fluid of rheumatoid arthritis patients was accompanied by a reduction of C-reactive protein levels. This serum protein, which is induced by IL-1 (or interleukin-6) has been shown to correlate with disease progression and bone damage in rheumatoid arthritis patients. This work suggests that suppression of lipoxygenase mediated IL-1 production breaks the chain of pathologic events associated with active synovitis and joint destruction in rheumatic diseases.

NSAID's do not inhibit IL-1 production nor do they reduce the elevated levels of acute phase proteins like C-reactive protein. This may explain why they only inhibit some of the pain and inflammation of rheumatic diseases but do not stop the progression of the disease. Other anti-rheumatic drugs like gold salts, anti-malarials and steroids, which do cause remission of rheumatoid arthritis, have also been demonstrated to reduce IL-1 synthesis. However, these drugs are toxic and have multiple pharmacologic activities. The compounds of the present invention which inhibit specific enzyme targets (cyclooxygenase and lipoxygenase) and thus IL-1 production have potential anti-rheumatic action.

A number of 1,5-diaryl-3-substituted pyrazoles are reported in the literature. Some of those pyrazoles have been reported to have pharmacological activity.

For example Fulmer et al., *J. Het. Chem.*, 17:799-800 (1980) report the synthesis of 1,3,5-triaryl pyrazoles, as do Foote et al., *J. Het. Chem.*, 7:89-92 (1970), Beam et al., *J. Het. Chem..* 9:183-185 (1972); Soliman et al., *J. Pharm. Sci.*, 70:606-610 (1981), and Barluenga et al., *J.C.S. Chem. Comm.*, 891 (1979). Soliman et al., *J. Pharm. Sci.*, 70:602-605 (1981) also report synthesis of 3-methyl-1,5-diarylpyrazoles in which the 1-position aryl is a phenylsulfonylurea or thiourea. Of the above reports, only the two reports by Soliman et al. discuss any pharmacological activity for the pyrazoles prepared or for analogs of those pyrazoles, and those materials are reported to have hypoglycemic activity.

Virmani et al., *Indian J. Chem., Sect. B*, 17B: 472-477 (1979) report the synthesis of 3-omega-alkylaminoalkyl pyrazoles among other compounds. The 1,5-diaryl-3-substituted pyrazoles reported contained a phenyl group at the 1-position, a 4-nitrophenyl at the 5-position, and a $(CH_2)_n$—$NHCH_3$ group at the 3-position, where n is 3,4 or 5 (3-5). This report stated that the compounds prepared were screened for a number of biological activities, with nine of the ninety-four numbered compounds synthesized having mild anti-inflammatory activity, two others having diuretic activity and two others having weak anti-cancer activity. The above-discussed 1,5-diaryl-3-Substituted pyrazoles were not among the compounds reported to have any pharmacological activity.

Vereshchagin et al., *Zh. Org. Khim..* 7:907-912 (1971) reported the synthesis of 1,5-diaryl-3-substituted pyrazoles. The 3-substituents were reported to be alkoxy alkylene in which the alkoxy radical was methoxy or phenoxy and the alkylene was methylene or isopropylene, while the 1,5-diaryl radicals were unsubstituted phenyl.

Jahn and Wagner-Jauregg, *Arzneim-Forsch. (Drug Res.)*, 24:494-499 (1974) reported the synthesis and some pharmacological activities of 1,5-diaryl-3-substituted-4,5-dihydropyrazoles. The aryl group at the 1-position for each reported compound was phenyl, while the 5-aryl substituent was reported to be phenyl, 4-methoxyphenyl, 3-methoxy-4-hydroxyphenyl, and 2-hydroxyphenyl. The before-mentioned pyrazoles were substituted at the 3-position by bonding to the 3-position of propionic acid or propiohydroxamic acid. These compounds were said to possess antirheumatic activity.

Shawali et al., *J. Het. Chem.*, 13:989-92 (1976); Shawali, *J. Het. Chem.*, 14:375-81 (1977); and Matsumoto et al., *Bull. Chem. Soc. Japan.* 47: 946-949 (1979) reported the synthesis of 1,5-diaryl-3-substituted pyrazoles, all of which also included a substituent other than hydrogen at the 4-position on the pyrazole ring. Exemplary 4-position substituents were reported to include cyano, amino, carboethyoxy, and phenylcarbonyl. These reports included no mention of biological activity of the compounds reported.

A series of benzimidoylpyrazoles was reported by Shrof et al., *J. Med. Chem.*, 24:1521-1525 (1981). These compounds were reported to possess activities of sulfonyl urea and biguanide hypoglcemics.

Biere et al., *Arch. Phar.*, 316:608-616 (1983) reported the synthesis of 1,4-diaryl-pyrazole-3-acetic acid derivatives, some of which also contained a an aryl substituent at the 5-position. The synthesized compounds were assayed for use as anti-inflammatory drugs in rats. The compounds assayed that also contained 5-position substituents were reported to be relatively inactive.

A further group of 1,5-diphenyl-4-substituted-pyrazole-3-acetic acids was reported by El-Sayed and Ohta, *Bull. Chem. Soc. Japan*, 46:1801-1803 (1973). Those compounds were utilized as intermediates in the synthesis of pyrazolo-[4,3-C]-pyridines. Another group of 1,5-diphenyl-4-substituted-pyrazoles, some of which also include methyl, phenyl and carboxymethyl groups at the 3-position, was reported in Al-Saleh et al., *J.C.S. Perkin I.* 642-645 (1981). The reports of El-Sayed and Ohta and those of Al-Saleh et al. make no mention of the pharmacological properties of the pyrazole derivatives reported. Another group of 1,5-diaryl-3,4-disubstituted pyrazoles and 4,5-dihydro-5-hydroxy pyrazoles was reported in Fusco and Croce, *Gazz. Chim. Ital.*, 101:703-272 (1971).

SUMMARY OF THE INVENTION

The present invention contemplates 1,5-diaryl-3-substituted pyrazoles, their use and a method of their synthesis. The compounds of the present invention are pharmacologically active in alleviating inflammation, and inhibit the cyclooxygenase enzyme pathway, the lipoxygenase enzyme pathway, or preferably both pathways.

In particular, the invention contemplates a substituted pyrazole compound having a structure that conforms to the formula

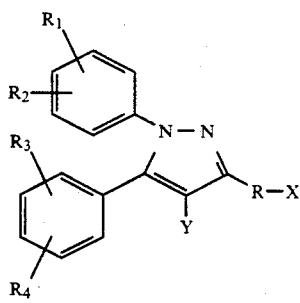

wherein $R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, ω-trifluoromethyl lower alkoxy, amino, acetamido, carboxy, alkylhydroxamic acid, or where $R_1$, $R_2$ or $R_3$, $R_4$ taken together with the phenyl group to which they are attached, form a naphthyl or substituted naphthyl group;

R is a straight, saturated or unsaturated hydrocarbon that contains 2-16 carbon atoms;

Y is hydrogen, bromo, chloro or lower alkyl having 1-4 carbon atoms;

and X is selected from the group consisting of carboxy, carboloweralkoxy, hydroxy, acetoxy, alkanoyloxy, lower alkoxy, lower alkyl carboxyl, oximo, cyano, amino, $C(O)—R_5$ and $—C(O)C(O)—R_5$ wherein $R_5$ is selected from the group consisting of hydrogen, alkyl, lower alkoxy, $NR_6R_7$ wherein $R_6$ and $R_7$ are the same or different and are selected from the group consisting of hydrogen, and lower alkyl, or $R_6$ or $R_7$ are selected from the group consisting of hydrogen, lower alkyl, lower alkoxy, hydroxy, lower acyloxy, benzyloxy, 2-hydroxy lower alkyl, lower alkyl carboxy, phenyl, substituted phenyl, pyridyl, thiazolyl, dihydrothiazolyl, ω-alkanoate, 5-tetrazolyl, $—OCO(CH_2)_nCOR_9$ wherein $R_9$ is $—OH$, $—ONa$, dialkylamino such as diethylamino and morpholino, and n is 2 or 3; $—OCOR_{10}$ wherein $R_{10}$ is $—CH_2NR_{11}R_{12}$ wherein $R_{11}$ and $R_{12}$ are alkyl, such as methyl, cycloalkyl such as cyclohexyl, or together are a heterocyclic ring such as N-methylpiperazino, $—OCOR_{10}$ wherein $R_{10}$ is $—CH_2Cl$, $—CH_2O$-loweralkyl or t-butyl, $—CH$-loweralkyl-$CO_2—Q$, wherein Q is lower alkyl or $—H$, acyl such as acetyl, propionyl or butyryl; $—NR_8OH$ wherein $R_8$ is hydrogen, $—CO$-loweralkyl, $—CO$-t-butyl, $—COC_7H_{15}$, $—CO$-phenyl, $SO_2$-lower alkyl, $—CO$-$CO_2$-lower alkyl, and $—COCONHOH$; $—NHR_{13}$ wherein $R_{13}$ is hydrogen, $—CO$-lower alkyl, $—CO$-t-butyl, $—COC_7H_{15}$, $—CO$-phenyl, $—SO_2$-lower alkyl, $—COCO_2$-lower alkyl, $—COCONHOH$, $—COCO_2H$, $COCON$(lower alkyl)OH, and PO(O-lower alkyl)$_2$; $—C(R_{14})=NNH$-2-thiazolino, $—CH(OH)R_{14}$ and $—C(O)R_{14}$ wherein $R_{14}$ is hydrogen, lower alkyl, phenyl and t-butyl; $—C(=NOH)NH_2$ and $—C(=NH)N(OH)$-lower alkyl and $O—NR_8R_9$ wherein $R_8$ and $R_9$ are the same or different and are selected from the group consisting of hydrogen, lower alkyl, phenyl and substituted phenyl;

with the provisos that:

(a) when Y is bromo or chloro, X is $—COOH$, $—CH_2OH$ or $—C(O)—R_5$ wherein $R_5$ is $NR_6R_7$ and $R_6$ is $—OH$ and $R_7$ is lower alkyl;

(b) at least one of $R_1$ and $R_2$ is other than hydrogen where (i) R—X is $(CH_2)_2CO_2H$ or $(CH_2)_2C(O)NHOH$ and (ii) $R_3$ and $R_4$ are 4-methoxy, 3-methoxy-4-hydroxy, 2-hydroxy and hydrogen; and (c) at least one of $R_1$ and $R_2$, or one of $R_3$ and $R_4$ is other than hydrogen where R—X together contains three saturated carbon atoms linked together by carbon-carbon bonds; and pharmaceutically acceptable salts thereof.

In preferred practice, $R_2$ and $R_4$ are hydrogen, and $R_1$ and $R_3$ are selected from the group consisting of halo, trifluromethyl, lower alkyl and lower alkoxy, especially methoxy. R preferably contains two carbon atoms. It is also preferred that the X be hydroxylower-alkyl, carboxy, a hydroxamic acid or a N-alkyl hydroxamic acid; i.e., that X be $C(O)NR_6R_7$ where $R_6$ is hydroxy and $R_7$ is hydrogen or lower alkyl or a N-alkyl hydroxamic acid; i.e. that X is $—C(O)NR_6R_7$ wherein $R_6$ is hydroxy or $—OC(O)CH_2Z$ where Z is dialkylamino or $—CH_2CO_2H$ and $R_7$ is hydrogen or lower alkyl.

The present invention also contemplates a pharmaceutical composition that comprises an anti-inflammatory amount of an above-described substituted pyrazole compound dispersed in a pharmaceutically acceptable carrier. The dose may be administered by topical, p.o., parenteral or aerosol routes. In preferred practice, that substituted pyrazole compound is capable of inhibiting both the cyclooxygenase and the lipoxygenase pathways in the amount present in the composition, when the composition is introduced into a mammal.

Further contemplated is a method for alleviating inflammation in a mammal exhibiting an inflammatory condition. That method comprises administering to that mammal a pharmaceutical composition that includes as the active ingredient an effective amount of an above-described substituted pyrazole compound dispersed in a pharmaceutically acceptable carrier for topical, oral, parenteral and aerosol administration.

A method for synthesizing a 1,5-diaryl-3-(omega-substituted lower alkyl)pyrazole is also contemplated. In accordance with this method, an aryl hydrazine or its acid addition salt is reacted with a 1-aryl-(omega-substituted)-alkyl-1,3-dione containing at least 4 carbons in the alkyl chain. A polar solvent is used that is substantially inert to the reaction conditions, as is the omega-substituent of the alkyl 1,3-dione. The resulting 1,5-diaryl-3-(omega lower alkyl substituted) pyrazole is thereafter preferably recovered, although it can be utilized in the form of its synthesis (crude form), as for further syntheses. Particularly preferred alkyl-1,3-dione derivatives contain 6 carbons in the alkyl chain and contain a hydroxy group as the omega-substituent.

The present invention provides several benefits and advantages.

A particular benefit of the invention is that it provides pharmacologically active compounds that are useful in treating inflammatory conditions.

A particular advantage of the present invention is that its synthetic method provides relatively high yields of 1,5-diaryl-3-(omega-substituted lower alkyl) pyrazole compounds.

Another benefit of the present invention is that some of its pharmacologically active compounds inhibit the clooxygenase enzyme pathway, thereby providing a further means for studying that biological process.

Another advantage of the present invention is that some of its pharmacologically active compounds inhibit the lipoxygenase enzyme pathway, thereby providing a further means for studying that biological process.

Still further benefits and advantages of the present invention will be apparent to those skilled in the art from the detailed description and examples that follow.

BRIEF DESCRIPTION OF THE DRAWINGS

FIG. 1 shows a graph illustrating the time course of immune-complex induced synovitis.

DETAILED DESCRIPTION OF THE INVENTION 1,5-Diaryl-3-substituted pyrazole compounds, pharmaceutical compositions containing a substituted pyrazole compound as an active ingredient, a method of treating a mammal exhibiting an inflammatory condition and a method of synthesizing the substituted pyrazole compound are contemplated herein.

In the above formula, $R_1$, $R_2$, $R_3$ and $R_4$ are substituents on phenyl rings that substitute for hydrogen atoms at positions 1 and 5 of the pyrazole ring. It is preferred that at least one of $R_1$ and $R_2$, and one of $R_3$ and $R_4$ be substituted at the 4-positions of their respective phenyl rings.

In examining the above structural formula to which the useful pyrazole compounds conform, it is noted that the $R_1$, $R_2$, $R_3$ and $R_4$ radicals and the X group can be a "lower" alkyl, "lower" alkoxy and the like. Groups and radicals referred to as "lower" denote that they possess 1 to about 6 carbon atoms. The same is true for "lower" groups and radicals that are substituent of the "lower" groups and radicals enumerated.

To the extent that X substituents are defined as being the same as those of $R_1$, $R_2$, $R_3$ and $R_4$, those commonly defined substituents are discussed immediately below. Additional X substituents that are not common to X and $R_1$, $R_2$, $R_3$ and $R_4$ are discussed thereafter.

Lower alkyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, octyl and the like.

Lower alkoxy radicals are oxygen ethers formed from a before-described lower alkyl group. Exemplary radicals include methoxy, ethoxy, propoxy, isopropoxy, n-butoxy, and the like.

Lower alkylthio radicals of $R_1$, $R_2$, $R_3$ and $R_4$ are sulfide ethers and are thus analogous to the oxygen ethers described above.

Halo radicals preferably include chloro and bromo, as well as fluoro and iodo.

Lower alkylsulfonyl radicals contain a before-described lower alkyl radical bonded to an $SO_2$ moiety that is itself also bonded to a phenyl ring. Exemplary lower alkylsulfonyl radicals thus include methylsulfonyl, ethylsulfonyl, 2-ethylbutylsulfonyl and the like.

An omega-trifluoromethyl lower alkoxy radical is a lower alkoxy radical as before described that additionally includes a trifluoromethyl group at a position farthest on the alkyl chain from the place of bonding to the phenyl ring. Exemplary of such radicals are the 2,2,2-trifluoroethoxy.

Naphthyl and substituted naphthyl radicals can replace an aryl group herein at either the 1- or 2-positions to provide 1-naphthyl or 2-naphthyl substituents, respectfully. Substituents on the naphthyl radicals can be any of those described herein as being useful aryl substituents. Exemplary substituted 1- and 2-naphthyls include 6-methoxy-2-naphthyl and the like.

Lower alkyl carboxy radicals are the before-described lower alkyl radicals that further include a carboxy group. Exemplary lower alkyl carboxy radicals include carboxymethyl, 2-carboxyhexyl and the like. Lower alkyl lower alkoxy carbonyl radicals are lower alkyl esters of lower alkyl carboxy radicals. Exemplary lower alkyl lower alkoxy carbonyl radicals include 3-iso-propoxycarbonylpropyl, 4-hexyloxycarbonylpentyl and the like.

A lower alkyl carbonyl radical contains a carbonyl group, a total of up to six carbon atoms, and with the portion of R to which it is linked, forms a ketone at the R/X junction. Exemplary lower alkyl carbonyl radicals include acetyl, propionyl 2-methylpropionyl, pentoyl and the like, which can also be named methyl carbonyl, ethyl carbonyl, isopropylcarbonyl and butylcarbonyl, respectively.

Radicals in which X is $C(O)-R_5$ wherein $R_5$ is lower alkoxy are carboxylic esters. These esters are preferably named by considering R—X to be a single substituent entity. Exemplary $R_5$ lower alkoxy groups are as before described, although methoxy and ethoxy are preferred. When $R_5$ is $NR_6R_7$ and $ONR_8R_9$, it is also useful to consider R—X as a substituent entity.

Lower hydroxy alkyl radicals of $R_6$ and $R_7$ are preferably 2-hydroxyethyl and 2-hydroxypropyl. Additionally useful lower hydroxy alkyl radicals include 4-hydroxybutyl and the like.

Substituted phenyl radicals that can comprise $NR_6R_7$ are the same as the substituted aryl groups described before wherein $R_1$, $R_2$, $R_3$ and $R_4$ comprise the substituents.

Pyridyl radicals are derivatives of pyridine and can be bonded to the nitrogen atom of $NR_6R_7$ at the 2-, 3- or 4-positions relative to the pyridine nitrogen.

R in the structural formula above is a straight, saturated or unsaturated hydrocarbyl radical that contains 2 to about 16 carbon atoms. In particularly preferred practice, the R—X radical together contains three saturated carbon atoms linked together by carbon-carbon bonds. In other preferred embodiments, R is unsaturated and contains 7–16 carbon atoms.

R is a hydrocarbon radical and therefore contains no elements other than carbon and hydrogen. Consequently, any element present in R—X that is not hydrogen or carbon is, by definition, part of the X radical.

Pharmaceutically acceptable, non-toxic acid addition salts of 1,5-diaryl-3-substituted-pyrazole compounds are useful herein, and can be formed by treatment of the pyrazole with an appropriate acid. Exemplary inorganic acids include hydrochloric, hydrobromic, sulfuric, phosphoric and the like acids. Exemplary organic acids include methanesulfonic, ethanesulfonic, benzenesulfonic and p-toluenesulfonic and the like acids. Conversely, the acid addition salt form can be converted to the free base form by treatment with alkali.

1,5-Diaryl-3-substituted pyrazole compounds can include a carboxylic acid and/or a hydroxamic acid, as already noted. Basic salts of those carboxylic and hydroxamic acids are also contemplated, and are formed by treatment of the acid with an appropriate, non-toxic, pharmaceutically acceptable alkaline reagent to form a carboxylate or hydroxamate cation salt. Exemplary non-toxic, pharmaceutically acceptable cation salts of such carboxylic and hydroxamic acids include sodium, potassium, zinc, aluminum, calcium and magnesium. These salts also readily form in aqueous solutions of the carboxylic and hydroxamic acids.

In preferred practice, $R_2$ and $R_4$ are hydrogen, and $R_1$ and $R_3$ are selected from the group consisting of halo and lower alkoxy, especially methoxy. The preferred $R_1$ and $R_3$ substituents are preferably at the 4-positions of their respective aryl (phenyl) rings.

It is preferred that R contain two carbon atoms and that X be carboxy, hydroxymethyl, a hydroxamic acid (N-hydroxy amide) or a N-lower alkyl hydroxamic acid (N-hydroxy-N-lower alkyl amide).

Specific, particularly preferred 1,5-diaryl-3-substituted pyrazole compounds are named hereinbelow, followed by a parenthesized, underlined numeral for ease of identification and correlation with the syntheses and anti-inflammation study described in detail hereinafter.

The preferred species of this invention include:
1. 3-[5-(4-chlorophenyl)-1-(4-methoxyphenyl)-3-pyrazolyl]-N-hydroxy-N-methylpropanamide, (3)
2. 5-(4-chlorophenyl)-3-(3-hydroxypropyl)-1-(4-methoxyphenyl) pyrazole, (2)
3. 5-(4-trifluoromethylphenyl)-3-(3-hydroxypropyl)-1-(4-methoxyphenyl) pyrazole, (56)
4. 1-(4-bromophenyl)-5-(4-chlorophenyl)-3-(3-hydroxypropyl) pyrazole, (35)
5. sodium 8-[5-(4-chlorophenyl)-1-(4-methoxyphenyl)-3-pyrazolyl]-5(Z)-octenoate, (32)
6. sodium 3-[5-(4-chlorophenyl)-1-(4-methoxyphenyl)-3-pyrazolyl]propanoate, (13)
7. 3-[5-(4-chlorophenyl)-1-(4-methoxyphenyl)-3-pyrazolyl]-N-tert-butyl-N-hydroxypropanamide, (57)
8. N-carboxymethyl-3-[5-(4-chlorophenyl)-1-(4-methoxyphenyl)-3-pyrazolyl] propanamide, (66)
9. 3-[5-(4-chlorophenyl)-1-(4-methoxyphenyl)-3-pyrazolyl]-N-hydroxy-N-isopropylpropanamide (81)
10. 3-[5-(4-chlorophenyl)-1-(4-methoxyphenyl)-3-pyrazolyl]-N-cyclohexyl-N-hydroxypropanamide (82)
11. 3-[5-(4-chlorophenyl)-1-(4-methoxyphenyl)-3-pyrazolyl]-N-ethyl-N-hydroxypropanamide (83)
12. 3-[5-(4-chlorophenyl)-1-(4-methoxyphenyl)-3-pyrazolyl]-N-hydroxy-N-phenylpropanamide (84)
13. 3-[5-(4-chlorophenyl)-1-(4-methoxyphenyl)-3-pyrazolyl]propylamine (96)
14. 3-[5-(4-chlorophenyl)-1-(4-methoxyphenyl)-3-pyrazolyl]propanal (11)
15. 5-(4-chlorophenyl)-3-(3-oximinopropyl)-1-(4-methoxyphenyl)pyrazole (26)
16. 3-(3-hydroxypropyl)-1-(4-methoxyphenyl)-5-(4-tolyl)pyrazole (55)

A pharmaceutical composition that comprises an anti-inflammatory amount of a before-discussed 1,5-diaryl-3-substituted pyrazole compound dispersed in a pharmaceutically acceptable carrier is also contemplated herein. The composition comprises a unit dosage of the substituted pyrazole compound.

The substituted pyrazole compounds of this invention are capable of inhibiting the lipoxygenase enzyme pathway and/or the cyclooxygenase (prostaglandin synthetase) enzyme pathway. In preferred practice, the substituted pyrazole compound of the pharmaceutical composition is capable of inhibiting both the lipoxyenase and the cyclooxygenase enzyme pathways in the amount at which that substituted pyrazole compound is present in the pharmaceutical composition, when that composition is introduced as a unit dose into an appropriate mammal such as a laboratory rat.

The term "unit dosage" and its grammatical equivalent is used herein to refer to physically discrete units suitable as unitary dosages for human patients and other warm blooded animals, each unit containing a predetermined effective, pharmacologic amount of the active ingredient calculated to produce the desired pharmacological effect in association with the required physiologically tolerable carrier, e.g., a diluent or a vehicle. The specifications for the novel unit dosage forms of this invention are dictated by and are directly dependent on (a) the unique characteristics of the active ingredient, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions and suspensions.

The active ingredient is referred to herein as being dispersed in the carrier. Thus, the dispersion formed can be a simple admixture, a non-settling dispersion as in the case of certain emulsions, or as an ultimate dispersion, a true solution.

The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligrams per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans. When the compounds are employed to treat rheumatoid arthritis the dosage range can be about 0.01 to about 160 mg/kg. The preferred dosage range is from about 0.5 to about 80 mg/kg.

As is seen from the data discussed hereinafter, orally administered unit doses containing about 1 to about 50 milligrams of a 1,5-diaryl-3-substituted pyrazole per kilogram of laboratory rat body weight (e.g., about 200 grams each) were useful in reducing inflammation. These results are contrary to those reported by Virmani et al., *Indian J. Chem., Sect. B,* 17:472–477 (1979) who reported compounds that are structurally similar to those described herein were not active as anti-inflammatory agents.

Physiologically tolerable carriers are well known in the art. Exemplary of liquid carriers are aqueous solutions that contain no materials in addition to the substituted pyrazole compound, or contain a buffer such as sodium phosphate at physiological pH value, saline and the like.

Liquid compositions can also contain liquid phases in addition to and to the exclusion of water. Exemplary of such additional liquid phases are glycerin and vegetable oils such as cottonseed oil.

Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such a cane or beet sugar, sodium saccharin, sodium cyclamate and the dipeptide methyl ester sweetener sold under the trademark NUTRASWEET (aspartame) by G. D. Searle Co.

A method for alleviating inflammation in a mammal exhibiting an inflammatory condition is also contemplated. The method comprises administering to that mammal an effective amount of a pharmaceutical composition that includes a unit dose of an active ingredient that is the before-described substituted pyrazole compound dispersed in a pharmaceutically acceptable carrier. The pharmaceutical composition is preferably maintained within the mammal until the substituted pyrazole compound is cleared from the mammal's body by natural means such as excretion or metabolism.

The pharmaceutical composition can be administered orally, topically or by injection, by means well known in the art. In preferred practice, the composition is administered orally as a tablet, capsule or aqueous dispersion.

Inasmuch as a pharmaceutical composition can be administered 3 to 4 times daily (per 24 hour period), the method of alleviating inflammation can include administering the pharmaceutical composition a plurality of times into the treated mammal over a time period of weeks, months and years. The pharmaceutical composition is administered a plurality of times to the mammal over a time period of thirty days, in preferred practice.

A method for synthesizing a 1,5-diaryl-(omega-substituted lower alkyl) pyrazole constitutes yet another aspect of the present invention. Here, an aryl hydrazine or its acid addition salt is admixed in an inert polar solvent with a 1-aryl-(omega-substituted)-alkyl-1,3-dione containing at least 4 carbons, and up to about 9 carbon atoms, in the alkyl chain to form a reaction mixture. The aryl hydrazine and the 1,3-alkyldione are preferably reacted in substantially stoichiometric amounts.

The omega-substituent of the 1-aryl-omega-substituted-alkyl-1,3-dione is substantially inert to the reaction conditions utilized for the cyclization reaction; i.e., the substituent does not itself react with any of the reactants or solvent during the cyclization reaction. Exemplary of useful substituents are hydroxy and lower alkoxy as before described. Hydroxy is particulary preferred as the omega substituent.

The aryl hydrazine and aryl-alkyl-1,3-dione are reacted in an inert polar solvent medium. Exemplary of such solvents are methanol, ethanol, isopropanol, pyridine, triethylamine and mixtures of those solvents.

The reaction mixture so formed is maintained with agitation, as by stirring, for a predetermined period of time for the 1-aryl-hydrazine and the 1-aryl-(omega-substituted)-alkyl-1,3-dione to react and form the desired 1,5-diaryl-3-(omega-substituted lower alkyl) pyrazole. The predetermined time period is typically about 1 to about 20 hours, depending upon the reactants, solvent and reaction temperature.

The cyclization reaction is normally carried out at ambient room temperature. The temperature typically rises somewhat during the cyclization, but is readily controlled. Temperatures above room temperature can also be utilized.

The resulting substituted pyrazole can be used as is in its crude form directly after the cyclization, as where a further reaction is to be carried out with it. Preferably however, the crude reaction product formed is recovered and purified as by crystallization or column chromatography prior to use in a further reaction or to alleviate inflammation.

Further reactions can be carried out on the omega-substituent of the pyrazole-3-lower alkyl group inasmuch as that substituent is substantially inert to the reaction conditions for cyclization and formation of the pyrazole ring, but need not be inert to all reaction conditions.

An exemplary, generalized reaction sequence is shown below in Scheme 1 where a 1-($R_3$, $R_4$-disubstituted phenyl)-6-hydroxy-hexan-1,3-dione and $R_1$,$R_2$-disubstituted phenyl hydrazine hydrochloride are reactants (A) and (B), respectively, that react to form 1-($R_1$,$R_2$-disubstituted phenyl)-5-($R_3$,$R_4$-disubstituted phenyl)-3-(3-hydroxypropyl)-pyrazole, I, wherein $R_1$,$R_2$,$R_3$ and $R_4$ are as previously defined. The parenthesized numerals beneath the structural formula of I refer to compounds of that structure that are exemplified hereinafter.

The reaction sequence shown thereafter in Scheme 2 relates to reactions carried out with specific compounds and in which R* is the 1-[5-(4-chlorophenyl)-1-(4-methoxyphenyl)-3-pyrazolyl]methylene group (as shown hereinafter); $R_1$-$R_7$ are as before described; lower case letters adjacent to reaction arrows indicate reaction conditions discussed thereafter below; and underlined numerals indicate specific compounds whose syntheses are described in detail hereinafter.

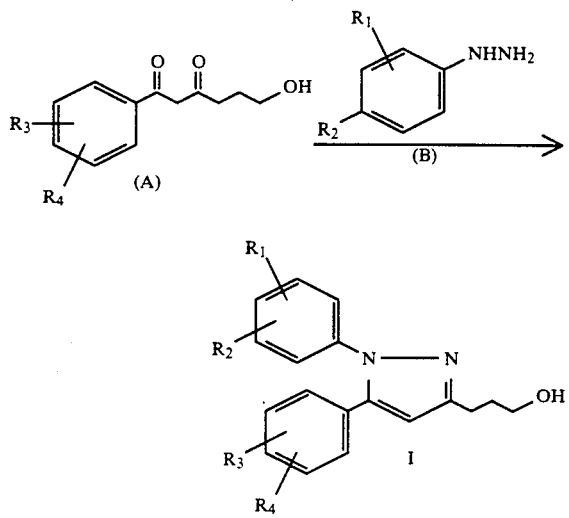

Scheme 1

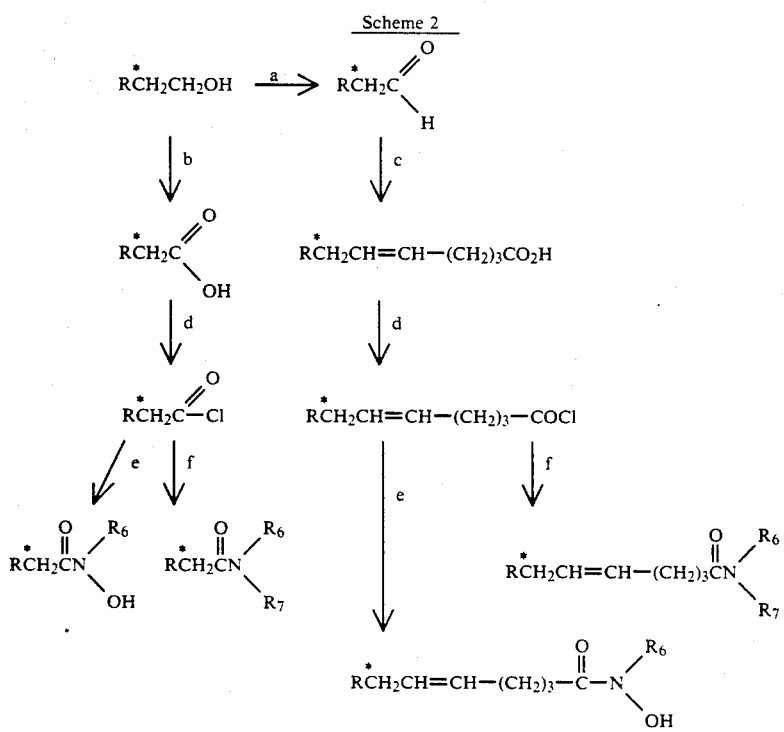

a, pyridinium chlorochromate; b, Jones Reagent; c, lithium hexamethyldisilazide/BrPh₃P(CH₂)₄CO₂H; d, oxalyl chloride; e, R₆NHOH; f, R₆R₇NH.

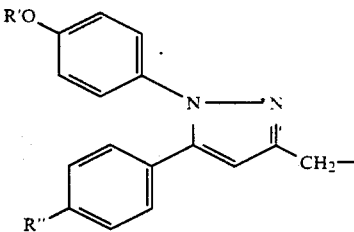

wherein R' is lower alkyl and R'' is a halogen selected from chloro, bromo, fluoro and iodo or lower alkyl.

Treatment of the appropriate aryl diketone A wherein $R_3$ and $R_4$ are defined as before with arylhydrazine B wherein $R_1$ and $R_2$ are defined as before gives the 1,5-diarylpyrazoles I that are isolated by recrystallization or chromatography on silica from the corresponding 1,3-diarylpyrazoles formed as minor products of the reaction.

The pyrazoles of formula I are oxidized to either the acid (e.g., 12) with, for example, Jones Reagent or to the aldehyde (e.g., 11) with, for example, pyridinium chlorochromate, as illustrated with compound 2; i.e., 5-(4-chlorophenyl)-3-(3-hydroxypropyl)-1-(4-methoxyphenyl)pyrazole. The olefinic acid 32 was obtained by treatment of aldehyde 11 with (4-carboxybutyl)triphenylphosphorane.

The appropriate acid chlorides were synthesized by treatment of acids of general formula 12 or 32 with a suitable acid chloride such as, for example, thionyl chloride or oxalyl chloride in a suitable solvent such as tetrahydrofuran (THF). The acid chlorides were then added as THF solutions to a solution of the appropriate alkylhydroxylamine hydrochloride [R₆NHOH(HCl)] in THF/water/triethylamine (THF/H₂O/Et₃N) to afford the alkylhydroxamic acids such as compounds 3, 58 and 41. The corresponding O-acylated products (e.g., 53 and 57) that may also form in the reaction were separated by either recrystallization or chromatography.

Similarly, treatment of the acid chlorides above with amines of general formula R₆R₇NH gave amides such as 28, 65 and 38, where $R_6$ and $R_7$ are as before defined.

Oxidation of compound 65 with Jones Reagent as above gave acid 66.

The remaining compounds of this invention were synthesized by standard methods from pyrazole alcohol 2, aldehyde 11 or acid 12 as shown in Scheme 3, below. The substituted pyrazole compounds with unsaturated side chains at the 3-position were prepared by reaction of aldehyde 11 with the appropriate Wittig reagent, as discussed specifically hereinafter and shown in Scheme 2, above. $R_1$–$R_7$, lower case letters and underlined numerals are as described for Schemes 1 and 2, before. R* in Scheme 3 is the 1-[5-(4-chlorophenyl)-1-(4-methoxyphenyl)-3-pyrazolyl-ethylene group, as shown.

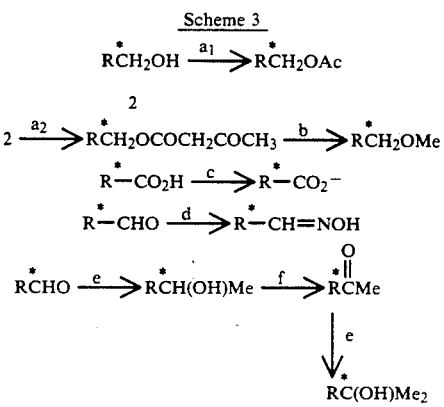

-continued
Scheme 3

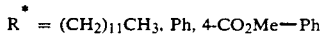

a₁, acetic anhydride/pyridine, a₂, 2,2,6-trimethyl-1,3-dioxen-4-one; b, NaH, methyl iodide; c, CH₂N₂; d, NH₂OH; e, methyl magnesium bromide; f, pyridinium chlorochromate; g, lauryltriphenyl phosphonium bromide [BrPh₃P(CH₂)₁₁CH₃] benzyltriphenylphosphonium chloride [PhCH₂⁺PPh₃Cl⁻]; (4-methoxycarbonylphenyl)-triphenylphosphonium chloride [4-CO₂-MePhCH₂P⁺Ph₃Cl⁻].

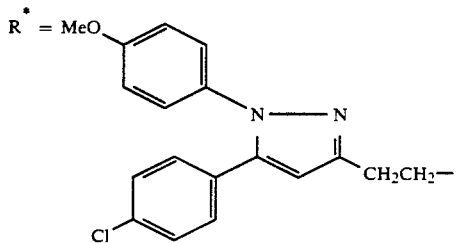

BEST MODES FOR CARRYING OUT THE INVENTION

Melting points (mp) were determined on a Thomas-Hoover apparatus, and are uncorrected. The infrared (IR) spectra were recorded on a Beckman Instruments IR-8 spectrophotometer and are expressed in reciprocal centimeters. Nuclear magnetic resonance (NMR) spectra for hydrogen atoms were measured in the indicated solvent with tetramethylsilane (TMS) as the internal standard on a Varian T-60A or an IBM WP-100 spectrometer. The values are expressed in parts per million downfield from TMS. Parenthesized, underlined hydrogens were assigned to the resonance positions immediately before the parentheses. EI and CI mass spectra were obtained on a Finnigan 1015D quadrupole mass spectrometer coupled to a Finnigan 9500 gas chromatograph or a Finnigan MAT 8230 Double Focusing high resolution mass spectrometer.

EXAMPLE 1

5-(4-Chlorophenyl)-3-(3-hydroxypropyl)-1-(4-methoxyphenyl) pyrazole (2)

4-Methoxyphenylhydrazine hydrochloride [35.0 grams (g), 0.20 moles] was added to CH₃OH [50 milliliters (ml)] containing pyridine (20 ml). An additional amount of CH₃OH (25 ml) was added to the thick resulting slurry. 1-(4-Chlorophenyl)-6-hydroxyhexan-1,3-dione (48.2 g, 0.20 moles), was added neat, followed by more CH₃OH (25 ml). The slurry was stirred at room-temperature for 1.5 hours, after which time the mixture was concentrated and taken up in CHCl₃ (300 ml). The CHCl₃ solution was washed with 1N HCl (300 ml), dried (Na₂SO₄), filtered, and concentrated. The oil was decolorized (Norit) in hot diethyl ether (Et₂O) (300 ml). The Et₂O solution was cooled, and crystallization from Et₂O (300 ml) afforded 2 (49.4 g). From the filtrate was obtained additional 2 (9.28 g), total yield 91%, mp 87.5°-88°. NMR (CDCl₃) 1.7-2.3 (m, 2H, CH₂CH₂CH₂), 2.55 (brs, 1H, OH), 2.80 (t, 2H, J=7 Hz, CH₂), 3.75 (t, 2H, J=6 Hz, CH₂O), 3.77 (s, 3H, OCH₃), 6.28 (s, 1H, C₄-H), 6.93 (ABq, 4H, J=12, 9, 4-OMe-C₆H₄), 6.9-7.3 (m, 4H, 4-Cl—C₆H₄); IR (KBr) 3320, 2920, 1495; MS, m/e 342 (M+), 312, 298 (100%);

Anal. Calcd. for C₁₉H₁₉ClN₂O₂:C,66.56,H,5.59;N,8.17
Found:C,66.54;H,5.76;N,8.02

The following general procedure was used for the preparation of 1,5-diaryl-3-(3-hydroxypropyl) pyrazoles of Tables 1 and 2 that follow.

The appropriate aryl hydrazine or hydrazine hydrochloride B [10 millimoles (Mm)] was dissolved in a solution of methanol (25 ml) containing pyridine (1 ml). The appropriately substituted 1-aryl-1,3-dione A (10 Mm) was admixed in a single portion. In a short time, the mixture warmed slightly, darkened, and became homogeneous. After stirring at ambient temperature for a time period of from 2 to 20 hours, the reaction mixture was worked up as follows: the mixture was concentrated in vacuo and taken up in diethyl ether (250 ml); the ether solution was washed with aqueous 1N HCl (200 ml), decolorized, dried (Na₂SO₄), filtered through a pad of celite, and concentrated in vacuo. The crude material was either purified by column chromatography (silica gel 60, 70-230 mesh, about 250 g, and elution with ether) to give the desired 1,5-diarylpyrazoles (I) or recrystallized directly without chromatography. In some cases the isomeric 1,3-diaryl isomer was also isolated in varying minor amounts, and eluted before I from the column.

TABLE 1

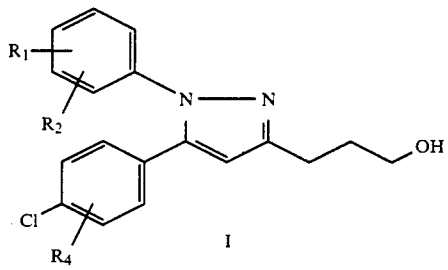

| Compound Number | R₁§ | Melting point | Analysis+ C, H, N | Mass spectrum m/e (M⁺) |
|---|---|---|---|---|
| 1 | 4-H | 105.5-106.5° | x x x | 312 (M⁺) |
| 2 | 4-OMe# | 87-88° | x x x | 342 (M⁺) |
| 4 | 4-Cl | 85-87° | x x x | 346 (M⁺) |
| 5 | 3-CF₃ | oil | x x x | 380 (M⁺) |
| 35 | 4-Br | oil | x x x | 390 (M⁺) |
| 36 | 4-SO₂CH₃ | 95-97° | x x x | 390 (M⁺) |
| 37 | 4-CH₃ | 92-94° | x x x | 326 (M⁺) |
| 42 | 3,4-diOMe | 113-114° | x x x | 372 (M⁺) |
| 46 | 3-OMe | oil | x x x* | 342 (M⁺) |
| 47 | 4-SMe | 82-84° | x x x | 358 (M⁺) |
| 48 | 4-NO₂ | foam | x x x** | 357 (M⁺) |
| 51 | 4-OC₅H₁₁ | oil | x x x | 398 (M⁺) |
| 52 | [6-MeO-naphth-2-yl] | foam | x x x | 392 (M⁺) |
| 60 | 2-CF₃ | oil | x x x | — |
| 61 | 4-OCH₂CF₃ | 87-89° | x x x | 410 (M⁺) |
| 8 | 3,4-diCl | oil | x x x | 380 (M⁺) |
| 22 | 2-OCH₃ | 78-82° | x x x | 312 (M⁺) |
| 62 | 4-F | 81-82° | x x x | 330 (M⁺) |
| 69 | 4-NH₂ | 210-213 | x x x*** | 327 (M⁺) |
| 70 | 4-CON(OH)Me | 98-100 | | 385 (M⁺) |

TABLE 1-continued

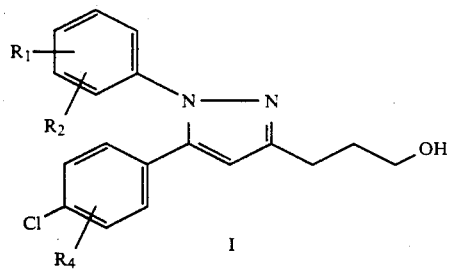

I

| Compound Number | R₁§ | Melting point | Analysis+ C, H, N | Mass spectrum m/e (M+) |
|---|---|---|---|---|
| 71 | 4-iPr | oil | x x x | 354 (M+) |

***dihydrochloride, monohydrate
**¼ hydrate
*hemihydrate
Me = CH₃
§$R_2$ and $R_4$ = H except for compounds 42 and 8, where $R_2$ = OMe and Cl, respectively.
+analysis within experimental error for C, H & N.

TABLE 2

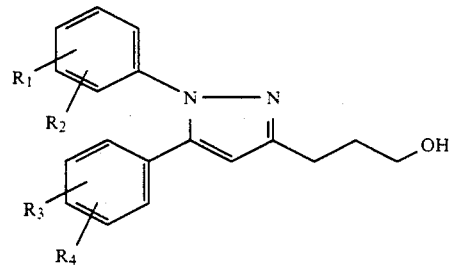

| Compound Name | R₁§ | R₃ | Melting point | Mass spectrum m/e (M=) |
|---|---|---|---|---|
| 9 | H | H | oil | 278 (M+) |
| 10 | 4-OMe# | H | oil | 308 (M+) |
| 18 | 2-OMe | H | oil | 308 (M+) |

TABLE 2-continued

| Compound Name | R₁§ | R₃ | Melting point | Mass spectrum m/e (M=) |
|---|---|---|---|---|
| 21 | 4-Cl | H | oil | 312 (M+) |
| 30 | 4-OMe | 4-F | 86–87.5° | 326 (M+) |
| 50 | 3,4-diOMe | H | oil | 338 (M+) |
| 54 | 4-OMe | 4-Ph## | foam** | 384 (M+) |
| 55 | 4-OMe | 4-Me | 94.5–96° | 322 (M+) |
| 56 | 4-OMe | 4-CF₃ | 73–75° | 376 (M+) |
| 68 | 4-OMe | 3,4-diCl | 56–58° | 376 (M+) |

**, &, # See Table 1 notes.
Ph = phenyl
§$R_2$ and $R_4$ = hydrogen except for compounds 50 and 68, where $R_2$ = OMe and $R_4$ = Cl, respectively.

Compounds in which $R_1$, $R_2$, $R_3$ and $R_4$ are all other than hydrogen can be synthesized by the above procedure. For example, when the aryl hydrazine B is 3,4-dimethoxyphenylhydrazine and the 1-aryl-1,3-dione A is 3,4-dichloro-4,6-dioxohexanoic acid, 5-(3,4-dichlorophenyl)-1-(3,4-dimethoxyphenyl)-3-(3-hydroxypropyl)-pyrazole is obtained.

TABLE 2'

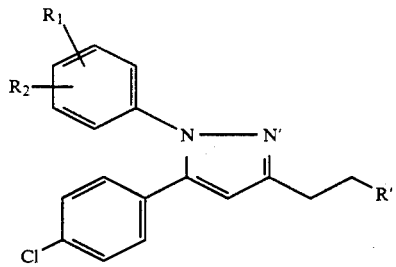

| Compound Number | R₁, R₂ | R' | Melting Point | Analysis C, H, N | Mass Spectrum m/e (M+) |
|---|---|---|---|---|---|
| 72 | 4-OEt | CO₂H | 123–125° | x x x | 370 |
| 73 | 4-OH | CO₂H | 239–241° | x x x | 342 |
| 74 | 3,4-diOMe | CO₂H | 153–154° | x x x | 386 |
| 75 | 4-OEt | CO₂Et | oil | x x x* | 398 |
| 76 | 4-OEt | —CON(OH)Me | foam | x x x** | 341 |
| 77 | 3,4-diOH | CO₂H | 179–180° | x x x⁴* | 358 |
| 78 | 3,4-diOMe | —CON(OH)Me | 162–163° | x x x | 415 |
| 103 | 2-OMe | —CO₂H | 135–137° | x x x | 356 |
| 104 | 2-OMe | —CON(OH)Me | 145–147° | x x x | 385 |

⁴*dihydrate
**¼ hydrate
*hemihydrate

TABLE 2''

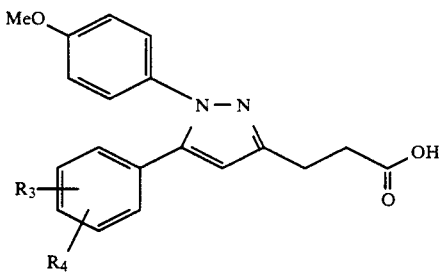

| Compound Number | R3,R4 | Melting Point | Mass Spectrum (m/e) | C, H, N |
|---|---|---|---|---|
| 105* | 4-Me | 145–147° | 336 (M+) | XXX |
| 106* | 3-Me | 109–110° | 336 (M+) | XXX |
| 107* | 3,4-di-Me | 141–142° | 350 (M+) | XXX |
| 108* | 2,4,6-tri-Me | 141–142° | 364 (M+) | XXX |
| 109* | 2-Me | 111–112° | 336 (M+) | XXX |
| 110* | 4-Et | 137–138° | 350 (M−) | XXX |

EXAMPLE 2

3-[5-(4-Chlorophenyl)-1-(4-methoxyphenyl)-3-pyrazolyl] propionic acid (12)

To a solution of the alcohol 2 [(0.92 g, 2.68 millimoles (mM)] in acetone (25 ml) was added a 2N $H_2Cr_2O_7$ (Jones Reagent) solution (3.02 ml, 6.04 mM) dropwise over a 10 minute time period. After stirring for 1 hour the reaction solution was decanted from the chromium precipitates on the sides of the reaction vessel. The reaction solution was concentrated in vacuo and taken up into ethyl acetate (EtOAc) (100 ml), washed with distilled $H_2O$ until the washes were clear, dried ($MgSO_4$), filtered, and concentrated in vacuo. Crystallization from $Et_2O$: hexane afforded 12 (0.88 g, 92%) as an off-white crystalline solid, mp=126°–128° C.

NMR: ($CDCl_3$) 2.7–3.2 (m, 4H, —$CH_2CH_2$—), 3.80 (s, 3H, —$OCH_3$), 6.30 (s, 1H, $C_4$-H), 6.7–7.5 (m, 8H, aromatic), 7.5–8.5 (1H, —COO$H$); IR (KBr) 1700; MS, m/e 356 (M+), 312, 311 (100%).

Anal. Calcd. for $C_{19}H_{17}ClN_2O_3$: C,63.95;H,4.80;N,7.85. Found: C,63.82;H,4.92;N,7.72.

EXAMPLE 3

Sodium 3-[5-(4-chlorophenyl)-1-(4-methoxyphenyl)-3-pyrazoyl] propanoate monohydrate (13)

To the acid 12 (1.0169 g, 2.85 mM) was added a 1.00N NaOH solution (2.85 ml, 2.85 mM) and distilled $H_2O$ (15 ml). The reaction mixture was stirred until it was homogeneous, and then lyophilized to afford 13 (1.08 g, 98%) as a white solid, with a mp greater than 300° C.

NMR ($CD_3OD$) 2.3–3.2 (m, 4H, —$CH_2$—$CH_2$—), 3.80 (s, 3H, —$OCH_3$), 6.47 (s, 1H, $C_4$—H), 6.7–7.4 (m, 8H, aromatic); IR (KBr) 3250, 1640.

Anal. Calcd. for $C_{19}H_{16}ClN_2NaO_3\cdot H_2O$:C,57.51;H,4.57;N,7.06
Found:C,57.19;H,4.33;N,6.98.

EXAMPLE 4

3-[5-(4-Chlorophenyl)-1-phenyl-3-pyrazolyl]propionic acid (17)

Following the procedure for compound 12 but substituting compound 1 for 2 afforded 17 (0.86 g, 68%) as a white crystalline solid, mp=138°–139° C.

NMR ($CDCl_5$) 2.6–3.2 (m, 4H, —$CH_2$—$CH_2$—), 6.30 (s, 1H, $C_4$—H); 6.4–7.5 (m, 10$\overline{H}$, aromatic and —COO$H$). IR (KBr) 3460, 1740; MS, m/e 326 (M+), 282, 281 (100%).

Anal. Calcd. for $C_{10}H_{15}ClN_2O_2$:C,66.16;H,4.63;N,8.57. Found:C,66.48;H,4.72;N,8.59.

EXAMPLE 5

3-[5-(4-Chlorophenyl)-1-(4-methoxyphenyl)-3-pyrazolyl]-N-hydroxy-N-methylpropanamide (3)

To a solution of the acid 12 (0.99 g, 2.77 mM) in tetrahydrofuran (THF) (20 ml) at 0° C., was added one drop of dimethyl formamide (DMF) and oxalyl chloride (0.29 ml, 33 mM). After 0.5 hours the cooling bath was removed and stirring was continued for an additional 0.5 hours. The reaction mixture was concentrated in vacuo to remove any excess oxalyl chloride, and the acid chloride of 12, was taken up into THF (10 ml).

To a solution of methylhydroxylamine hydrochloride (0.35 g, 4.16 mM) and triethylamine ($Et_3N$) (1.55 ml, 11.10 mM) in THF, $H_2O$ (10 ml:5 ml) at 0° C., was added the THF solution of the acid chloride dropwise over a 5 minutes period. The cooling bath was removed, and the reaction mixture was stirred for 1 hour, diluted to 100 ml with EtOAc, washed with $H_2O$, dried ($MgSO_4$), filtered, and concentrated in vacuo. Chromatography (Baker silica gel, 45 g) of the residue with EtOAc as eluent, followed by crystallization from $Et_2O$ afforded pure 3 (0.70 g, 65%), mp=113°–115° C. Further recrystallization from ethyl acetate afforded white crystalline solid, m.p. 125°–26° C.

NMR: ($CDCl_3$) 2.7–3.5 (m, 4H, —$CH_2CH_2$—), 3.18 (broad s, 3H, —N—$CH_3$), 3.83 (s, 3H, —$OCH_3$), 6.30 (s, 1H, $C_4$—H), 6.7–7.4 (m, 8H, aromatic), 10.67 (broad s, 1H, —N—OH); IR (KBr) 3160, 1640; MS, m/e 385 (M+), 339 (100%).

Anal. Calcd. for $C_{20}H_{20}ClN_3O_3$:C,62.25;H,5.22;N,10.89.
Found:C,62.60;H,5.18;N,10.82.

TABLE 2'''

| Compound Number | R1,R2 | R3,R4 | Melting Point | Mass Spectrum (m/e) | C,H,N |
|---|---|---|---|---|---|
| 111 | 4-OMe | 4-Me | 119–121° | 365 (M+) | XXX* |
| 112 | 4-Cl | 4-OMe | 158–160° | 385 (M+) | XXX |
| 113 | 4-OMe | 4-OMe | 104–105° | 381 (M+) | XXX |
| 114 | 4-OMe | 4-H | foam | 351 (M+) | XXX* |

TABLE 2'''-continued

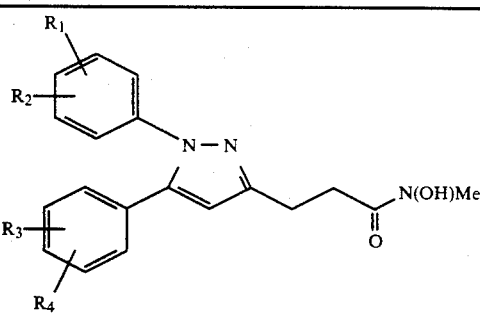

| Compound Number | R1,R2 | R3,R4 | Melting Point | Mass Spectrum (m/e) | C,H,N |
|---|---|---|---|---|---|
| 115 | 4-OMe | 3-Me | 137–138° | 365 (M+) | XXX |
| 116 | 4-OMe | 3,4-di-Me | 130–131° | 379 (M+) | XXX |
| 117 | 4-OMe | 2,4,6-tri-Me | 133–134° | 393 (M+) | XXX |
| 118 | 4-OMe | 2-Me | 117–118° | 365 (M+) | XXX |
| 119 | 4-OMe | 4-Et | 72–74° | 379 (M+) | XXX |

*½ hydrate

TABLE 2''-AP

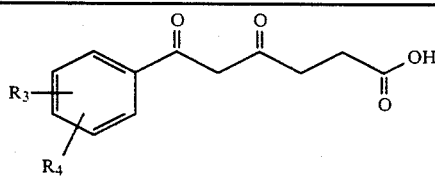

| Compound Number | R3,R4 | Melting Point | Mass Spectrum (m/e) | C,H |
|---|---|---|---|---|
| 120 | 4-Me | 139–141° | 234 (M+) | XX |
| 121 | 3-Me | 92–94° | 234 (M+) | XX |
| 122 | 3,4-di-Me | 98–100° | 248 (M+) | XX |
| 123 | 2-Me | 139–140° | 234 (M+) | XX |
| 124 | 4-Et | 114–115° | 248 (M+) | XX |
| 125 | 4-Cl | 137–139° | 254 (M+) | XX |
| 126 | 4-F |  | 238 (M+) | XX |
| 127 | 3,4-di-Cl | 87–90° | 288 (M+) | XX |
| 128 | H | 102–105° | 220 (M+) | XX |

The following general procedure was used for the preparation of the 1,5-diaryl-3-pyrazole propionic acids of Table 2''.

A mixture of the appropriate 6-aryl-4,6-diketohexanoic acid (0.1 Mole) from Table 2''-AP in methanol (750 ml) containing Et₃N (0.2 Mole) was treated with 4-methoxyphenylhydrazine hydrochloride (17.4 g, 0.1 Mole) at room temperature for 1 hour. If the reaction was incomplete at this point, it was refluxed until complete. The resulting darkened solution was evaporated in vacuo and taken up in Et₂O (700 ml); the ether solution was washed with aqueous 1N HCl (350 ml), brine, dried (Na₂SO₄), decolorized, evaporated in vacuo and recrystallized from Et₂O.

The compounds of Table 2'' were synthesized directly from the appropriate 4,6-diketohexanoic acid as described below.

Synthesis of 6-Aryl-4,6-diketohexanoic acids

The compounds of Table 2''-AP were synthesized by the following general procedure. To a reaction vessel containing anhydrous THF (250 ml) and diisopropylamine (14 ml, 0.1 Mole) stirring under nitrogen at 0° C. was added by syringe, n-BuLi (1.6M, 62.5 ml, 0.1 Mole). The vessel was then cooled to −7B° C. Alternatively, lithium hexamethyldisilazide (0.1 Mole) may be employed as the base in place of lithium diisopropylamide.

The appropriately substituted acetophenone (0.1 Mole) in anhydrous THF (50 ml) was added and the resulting solution allowed to stir for 30 minutes at −78° and succinic anhydride (4.0 g, 0.04 mole) in THF (100 ml) was added via syringe. The solution was allowed to stir for 1 hour at −78°, warmed to room temperature for 1 hour and poured into 5% HCl (250 ml). The mixture was extracted with Et₂O (2×300 ml) and the combined ether extract was extracted with 10% NaOH (100 ml). The NaOH layer was separated and acidified with 4N HCl, and reextracted with Et₂O (2×300 ml). The combined ether layers were dried (Na₂SO₄), filtered and concentrated in vacuo. The resultant residues were recrystallized from the appropriate solvent to give the compounds of Table 2''-AP.

EXAMPLE 6

3-[5-(4-Chlorophenyl)-1-(4-methoxyphenyl)-3-pyrazolyl]-N-hydroxy-N-methylpropanamide sodium salt monohydrate(3a)

To hydroxamic acid 3 (0.6052 g, 1.57 mM) was added 1.00N NaOH solution (1.57 ml, 1.57 mM) and distilled H₂O (3 ml). The reaction mixture was stirred for 10 minutes at which time it was homogeneous. Lyophilization afforded pure 3a (0.64 g, 97%) as a white hygroscopic solid, mp=100°–110° C. (decomposed).

NMR: (CD₃OD) 2.3–3.4 (m, 4H, —CH₂CH₂—), 2.92 (broad s, 3H, —NCH₃), 3.78 (s, 3H, —OCH₃), 6.47 (s, 1H, C₄—H), 6.7–7.6 (m, 8H, aromatic); IR (KBr) 3420, 1600; MS, m/e 384 (M-Na).

Anal. Calcd. for C₂₀H₁₉ClN₃NaO₃.H₂O:C,56.40;H,4.97;N,9.87.
Found:C,56.24;H,4.53;N,9.70.

EXAMPLE 7

0-[2-[5-(4-Chlorophenyl)-1-(4-methoxyphenyl)-3-pyrazolyl] ethyl-carbonyl]-N-methylhydroxylamine (53)

The procedure to synthesize compound 3 was repeated on a twenty-fold scale.

Chromatography of the crude reaction mixture (Merck Silica Gel 60; 230–400 mesh, 150 g) with CH₃OH:CHCl₃ (3:97) as eluent, separated 3 from a mixture with the less polar component (2.5 g, Rf=0.18).

Chromatography (Merck Silica Gel 60; 230–400 mesh, 75 g) of this mixture with Et₂O as eluent, and crystallization from Et₂O:hexane afforded 53 (0.81 g, 3.7%) as a white crystalline solid, mp=80°–81° C. (sharp).

NMR: (CDCl₃) 2.83 (d, 3H, J=7.5 Hz, —NHCH₃), 2.6–3.3 (m, 4H, —CH₂CH₂—), 3.83 (s, 3H, —OCH₃), 6.33 (s, 1H, C₄—H), 6.7–7.4 (m, 4H, aromatic), 7.55 (q, J=7.5 Hz, 1H, —NHCH₃); IR (KBr) 3200, 1740; MS (20 eV EI), m/e 356, 339 (100%), 311, 297.

Anal. Calcd. for C₂₀H₂₀ClN₃O₃:C,62.25;H,5.22;N,10.89.
Found:C,62.31;H,5.21;N,10.88.

EXAMPLE 8

N-Carboxymethyl-3-[5-(4-chlorophenyl)-1-(4-methoxyphenyl)-3-pyrazolyl]propanamide (66)

Following the procedure of Example 5, but substituting glycine for methylhydroxylamine hydrochloride afforded 66 (1.98 g, 67.4%), as a white crystalline solid, melting point = 185.5°–187.5° C.

NMR (DMSO-d₆) 2.4–2.7 (m, 2H, —CH₂CH₂CON—), 2.7–3.0 (m, 2H, —CH₂CH₂CON—), 3.78 (s, 3H, —OCH₃), 3.78 (d, J=5.5 Hz, 2H, —NHCH₂COOH), 6.53 (s, 1H, C₄—H), 6.7–7.6 (m, 8H, aromatic), 8.29 (broad t, J=5.5 Hz, 1H, CONH—CH₂COOH); IR (KBr) 3360, 1725, 1665; MS, m/e 413 (M+), 311 (100%).

Anal. Calcd. for C₂₁H₂₀ClN₃O₇:C,60.94;H,4.87;N,10.15. Found:C,60.64;H,4.87;N,10.01.

EXAMPLE 9

3-[5-(4-Chlorophenyl)-1-phenyl-3-pyrazolyl]-N-hydroxy-N-methyl propanamide (67)

Following the procedure described in Example 5 but substituting compound 17 for compound 12 afforded 67 (1.24 g, 78.0%) as a white crystalline solid, mp=155°–156° C.

NMR (CDCl₃) δ 2.5–3.5 (m, 4H, —CH₂CH₂—), 3.20 (s, 3H, —N(CH₃)OH), 6.33 (s, 1H, C₄H), 7.0–7.7 (m, 9H, aromatic), 10.37 (broad s, 1H, —N(CH₃) OH); IR (KBr): 3120, 1650; MS, m/e 355 (M+), 309 (100%).

Anal. Calcd. for C₁₉H₁₈ClN₃O₂:C,64.13;H,5.10;N,11.81. Found:C,64.17;H,5.45;N,11.51.

EXAMPLE 10

3-[5-(4-Fluorophenyl)-1-(4-methoxyphenyl)-3-pyrazolyl]-N-hydroxy-N-methyl propanamide (45)

Following the procedure described in Example 5, but substituting compound 30 for compound 12 afforded 45 (1.21 g, 83%) as an off-white crystalline Solid, mp=151°–154° C.

NMR (CDCl₃) 2.7–3.5 (m, 4H, —CH₂CH₂—), 3.20 (broad s, 3H, —NCH₃), 3.83 (s, 3H, —OCH₃), 6.30 (s, 1H, C₄—H), 6.7–7.4 (m, 8H, aromatic), 10.4–10.9 (broad s, 1H, —NOH); IR (KBr): 3140, 1650; MS (20 eV EI), m/e 369 (M+), 340, 323 (100%).

Anal. Calcd. for C₂₀H₂₀FN₃O₃:C,65.03;H,5.46;N,11.38. Found:C,64.87;H,5.59;N,11.05.

EXAMPLE 11

Following the procedure described in Example 5, the following compounds were synthesized.

| Compound Number | R₃ | R' | Melting Point | Analysis C, H, N | Mass Spectrum m/e (M+) |
|---|---|---|---|---|---|
| 81 | Cl | iPr | 80–83° | x x x* | 413 |
| 82 | Cl | cyclohexyl | 74–76° | x x x | 453 |
| 83 | Cl | Et | 113–114° | x x x | 399 |

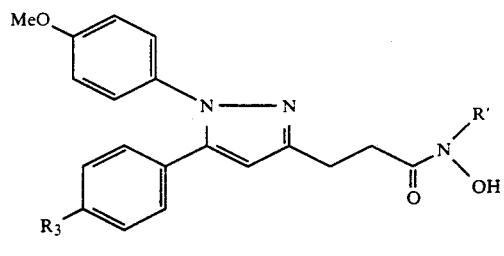

| Compound Number | R₃ | R' | Melting Point | Analysis C, H, N | Mass Spectrum m/e (M+) |
|---|---|---|---|---|---|
| 84 | Cl | phenyl | 113.5–114.5 | x x x | 447 |
| 79 | CF₃ | Me | foam | x x x²* | 419 |

*¹ C₆H₁₄
²*¹ H₂O

EXAMPLE 12

3-[5-(4-Chlorophenyl)-1-(4-methoxyphenyl)-3-pyrazolyl]-N-hydroxypropanamide (29)

To a solution of the acid 12 (0.97 g, 2.72 mM) in THF (20 ml) at 0° C., was added one drop of DMF (catalyst) and oxalyl chloride (0.28 ml, 3.26 mM). After 0.5 hour the cooling bath was removed and stirring was continued for 0.5 hour. The reaction mixture was concentrated in vacuo to remove any excess oxalyl chloride, and the remaining crude acid chloride, of acid 12, was taken up in THF (10 ml).

To a solution of hydroxylamine hydrochloride (0.28 g, 4.08 mM) and Et₃N (1.52 ml, 10.9 mM) in THF:H₂O (10 ml:5 ml) at 0° C., was added the crude acid chloride solution, dropwise over a 5 minute period. The cooling bath was removed, and the reaction mixture was stirred for 1 hour, diluted to 100 ml volume with EtOAc, washed with H₂O, dried (MgSO₄), filtered, and concentrated in vacuo. Crystallization from Et₂O afforded 29 (0.88 g, 87%) as a white crystalline solid, mp =154°–156° C.

NMR (CDCl₃) 2.4–3.4 (m, 4H, —CH₂CH₂—), 3.80 (s, 3H, —OCH₃), 6.30 (s, 1H, C₄—H), 6.3–7.5 (m, 9H, aromatic and —NH—). IR (KBr): 3260, 1665; MS, m/e 371 (M+), 353, 339, 311, 298 (100%).

Anal. Calcd. for C₁₉H₁₈ClN₃O₃:C,61.37;H,4.88;N,11.30. Found:C,61.36;H,5.05;N,10.97.

EXAMPLE 13

0-[2-[5-(4-Chlorophenyl)-1-(4-methoxyphenyl)-3-pyrazolyl]ethylcarbonyl]-N-tert-butylhydroxylamine (57); and 3-[5-(4-chlorophenyl)-1-(4-methoxyphenyl)-3-pyrazolyl]-N-tert-butyl-N-hydroxypropanamide (58)

To a solution of the acid 12 (0.99 g, 2.77 mM) in THF (30 ml) at 0° C., was added one drop of DMF and oxalyl chloride (0.29 ml, 3.33 mM). After stirring for 0.5 hour the cooling bath was removed and stirring was continued for 0.5 hour. The reaction mixture was concentrated in vacuo to a volume of 10 ml, and added dropwise to a solution of N-(tert-butyl)hydroxylamine (HCl) (0.52 g, 4.16 mM) and Et₃N (1.56 ml, 11.1 mM) in THF:H₂O (12 ml:6 ml) at 0° C. The reaction mixture was stirred for 1 hour, diluted to 100 ml with EtOAc, washed with H$_2$O, dried (MgSO$_4$), filtered and concentrated in vacuo. The residue was combined with that from a similar run on a 2.72 mM scale.

Chromatography (Merck Silica Gel 60; 230–400 mesh, 72 g) with Et$_2$O:hexane (4:1) as eluent afforded 57, crystallized from cold Et$_2$O:hexane (1.19 g, 51%) as a white crystalline solid, mp=73°–74.5° C. and 58 recrystallized from EtOAc:Et$_2$O (0.63 g, 27%) as a white crystalline solid, mp=137°–138° C.

Compound 57, NMR (CDCl$_3$) 1.10 (s, 9H, —C(CH$_3$)$_3$), 2.7–3.4 (m, 4H, —CH$_2$CH$_2$—), 3.80 (s, 3H, —OCH$_3$), 6.32 (s, 1H, C$_4$—H), 6.7–7.5 (m, 8H, aromatic); IR (KBr) 3480, 1730; MS (20eV EI), m/e 339 (100%), 311, 297.

Anal. Calcd. for C$_{23}$H$_{26}$ClN$_3$O$_3$: C, 64.55; H, 6.12; N, 9.82. Found: C, 64.41; H, 6.19; N, 9.71.

Compound 58, NMR (CDCl$_3$) 1.25 (s, 9H, —C(CH$_3$)$_3$), 2.7–3.4 (m, 4H, —CH$_2$CH$_2$—), 3.83 (s, 3H, —OCH$_3$), 6.33 (s, 1H, C$_4$—H), 6.7–7.5 (m, 8H, aromatic), 10.08 (s, 1H, —N—OH). IR (KBr) 3460, 3130, 1620, 1590; MS (20eV EI), m/e 427 (M$^+$), 339 (100%), 311, 297.

Anal. Calcd. for C$_{23}$H$_{20}$ClN$_3$O$_3$: C, 64.55; H, 6.12; N, 9.82. Found: C, 64.62; H, 6.38; N, 9.72.

EXAMPLE 14

3-[5-(4-Chlorophenyl)-1-(4-methoxyphenyl)-3-pyrazolyl] propanal (11)

To a suspension of pyridinium chlorochromate (10.02 g, 46.5 mM) in CH$_2$Cl$_2$ (500 ml) was added the alcohol 2, (5.09 g, 15.5 mM). After stirring overnight, the reaction mixture was concentrated in vacuo to a volume of about 200 ml, and diluted to 1 liter with Et$_2$O. This solution was filtered through celite, and the filter cake was washed with Et$_2$O (2×200 ml). The filtrate and the washes were combined and concentrated in vacuo. Chromatography (120 g, Baker silica gel) of the residue with Et$_2$O:hexane (2:1) as eluent, and crystallization from Et$_2$O afforded pure 11, (0.88 g, 17%) as a white crystalline solid, mp=101°–102° C.

NMR (CDCl$_3$) 2.8–3.2 (m, 4H, —CH$_2$CH$_2$CHO), 3.85 (s, 3H, —OCH$_3$), 6.32 (s, 1H, C$_4$—H), 6.7–7.4 (m, 8H, aromatic), 9.93 (t, J=1 Hz, 1H, —CHO); IR (KBr) 1715; MS, m/e 340 (M$^+$), 312 (100%).

Anal. Calcd. for C$_{19}$H$_{17}$ClN$_2$O$_2$: C, 66.96; H, 5.03; N, 8.22. Found: C, 66.72; H, 5.12; N, 8.13.

EXAMPLE 15

Sodium 8-[5-(4-Chlorophenyl)-1-(4-methoxyphenyl)-3-pyrazolyl]-5(Z)-octenoate (32)

To a solution of hexamethyldisilazane (5.25 ml, 24.9 mM) in THF (125 ml) at +5° C. was added 1.46 M n-butyl lithium (n-BuLi) (16.3 ml, 23.8 mM). The cooling bath was removed after 15 minutes and (4-carboxybutyl)triphenylphosphonium bromide (5.17 g, 11.7 mM) was added. Stirring was continued for 45 minutes and the aldehyde 11 (3.61 g, 10.6 mM) was added. After stirring for 1 hour, the reaction solution was diluted to a 600 ml volume with EtOAc and extracted with H$_2$O (2×200 ml). The extracts were combined, acidified with 3N HCl, and extracted with EtOAc (2×200 ml). The EtOAc extracts were combined, dried (Na$_2$SO$_4$), filtered and concentrated in vacuo. Chromatography of the remaining residue (Baker silica gel, 160 g) with Et$_2$O as eluent afforded the acid (3.39 g, 75%) as a clear yellow oil.

To the neat acid (0.57 g, 1.34 mM) was added a 1.00N NaOH solution (1.34 ml, 1.34 mM) and a small amount of water. After stirring overnight, the reaction solution was lyophilized to afford 32 (0.60 g, 95%) as a white solid.

Acid, NMR (CDCl$_3$) 1.4–3.1 (m, 10H, —CH$_2$CH$_2$CH=CH(CH$_2$)$_3$COOH), 3.80 (s, 3H, —OCH$_3$), 5.2–5.7 (m, 2H, —CH=CH—), 6.33 (s, 1H, C$_4$—H), 6.7–7.5 (m, 8H, aromatic); MS (20 eV EI), m/e 426 (M+2), 424 (M$^+$), 365, 351, 337, 298 (100%).

Compound 32, NMR (CD$_3$OD) 1.4–3.1 (m, 10H, —CH$_2$CH$_2$CH=CH(CH$_2$)$_3$—), 3.80 (s, 3H, —OCH$_3$), 5.2–5.7 (m, 2H, —CH=CH—), 6.45 (s, 1H, C$_4$—H), 6.7–7.5 (m, 8H, aromatic); IR (KBr) 3440, 1565; MS, m/e 423 (M-Na).

Anal. Calcd. for C$_{24}$H$_{24}$ClN$_2$NaO$_3$(1.25 H$_2$O): C, 61.40; H, 5.69; N, 5.97. Found: C, 61.60; H, 5.46; N, 5.51.

EXAMPLE 16

8-[5-(4-Chlorophenyl)-1-(4-methoxyphenyl)-3-pyrazolyl]-N-hydroxy-N-methyl-5(Z)-octenamide (41)

Following the procedure described in Example 5, but substituting the acid for 12 afforded 41 (0.94 g, 62%) as a clear colorless oil.

NMR (CDCl$_3$) 1.5–3.5 (m, 14H, —(CH$_2$)$_2$—CH=CH—(CH$_2$)$_3$CON(CH$_3$)OH), 3.80 (s, 3H, —OCH$_3$), 5.3–5.7 (m, —CH=CH—, 2H), 6.30 (s, 1H, C$_4$—H), 6.7–7.4 (m, 8H, aromatic); IR (neat): 3160, 1630; MS (20 eV EI), m/e 455 (M+2), 453 (M$^+$), 407, 379, 365, 298 (100%).

Anal. Calcd. for C$_{25}$H$_{28}$ClN$_3$O$_3$: C, 66.14; H, 6.22; N, 9.26. Found: C, 65.78; H, 6.55; N, 8.93.

EXAMPLE 17

3-[5-(4-Chlorophenyl)-1-(4-methoxyphenyl)-3-pyrazolyl]-N,N-diethylpropanamide (28)

To a solution of the acid 12 (1.01 g, 2.83 mM) in THF (25 ml) at 0° C., was added one drop of DMF and oxalyl chloride (0.30 ml, 3.40 mM). After 0.5 hours the cooling bath was removed and stirring was continued for 0.5 hour. The reaction mixture was concentrated in vacuo to remove the excess oxalyl chloride, and the remaining acid chloride was diluted with THF (25 ml) and cooled to 0° C. To this solution diethylamine (1.17 ml, 11.32 mM) was added dropwise over a 5 minute period. After stirring for 1 hour, the reaction mixture was diluted to 100 ml with Et$_2$O, washed with H$_2$O, dried (MgSO$_4$), filtered and concentrated in vacuo. Crystallization from Et$_2$O afforded 28 (0.98 g, 84%) as a yellow crystalline solid, mp=111°–112° C.

NMR (CDCl$_3$) 1.13, 1.17 (2t, J=7 Hz, 6H, —N(CH$_2$CH$_3$)$_2$), 2.5–3.8 (m, 8H, —CH$_2$CH$_2$— and —N(CH$_2$CH$_3$)$_2$), 3.80 (s, 3H, —OCH$_3$), 6.30 (s, 1H, C$_4$—H), 6.7–7.4 (m, 8H, aromatic); IR (KBr) 1630; MS (20eV EI), m/e 411 (M$^+$), 311 (100%).

Anal. Calcd. for C$_{23}$H$_{26}$ClN$_3$O$_2$: C, 67.06; H, 6.36; N, 10.20. Found: C, 67.14; H, 6.34; N, 9.95.

EXAMPLE 18

Compounds of Table 3

Following the procedure of Example 17, but substituting $NH_4OH$, 4-aminophenol, O,N-dimethylhydroxylamine hydrochloride, 2-aminophenol, 2-aminothiophenol, 2-aminopyridine and ethanolamine for diethylamine gave the compounds of Table 3.

TABLE 3

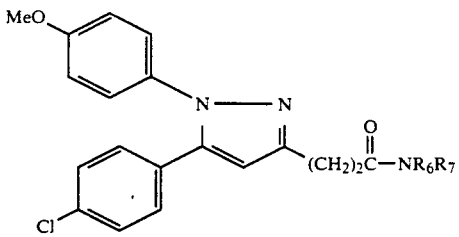

| Compound Number | $NR_6R_7$ | Melting Point | Mass Spectrum m/e | C,H,N |
|---|---|---|---|---|
| 31 | —$NH_2$ | 145–146° | 355 (M+) | XXX |
| 34 | —NH—C6H4—OH | 223–226° | 447 (M+) | XXX |
| 44 | —N($CH_3$)$OCH_3$ | 136–137° | 399 (M+) | XXX |
| 40 | —NH-(2-pyridyl) | 176–177° | 432 (M+) | XXX |
| 63 | —NH—C6H4—OH (ortho) | 198–200° | 448 (M+) | XXX |
| 64 | —NH—C6H4—SH (ortho) | 157.5–159° | 468 (M+) | XXX |
| 65 | —$NHCH_2CH_2OH$ | 115–118°* | 399 (M+) | XXX* |

*¼ hydrate

In addition, following the procedure of Example 17, the following were synthesized.

| Compound Number | $NR_6R_7$ | Melting Point | Mass Spectrum m/e | C,H,N |
|---|---|---|---|---|
| 85 | —NH—C(=S)—NH (thiazoline) | 227–228° | 440 (M+) | XXX* |
| 86 | —NH—C6H4—OMe | 187.5–189° | 461 (M+) | XXX* |
| 87 | $\underset{N}{H}$ $CH_2CO_2Et$ | 104–105.5° | 441 (M+) | XXX |
| 88 | $\underset{N}{H}$ $CH_2CONHOH$ | 160–162° | 428 (M+) | XXX* |
| 89 | $\underset{N}{H}$ $CH_2CON(OH)Me$ | 180–182° | 442 (M+) | XXX |

-continued

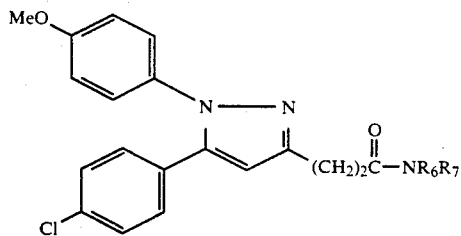

| Compound Number | NR$_6$R$_7$ | Melting Point | Mass Spectrum m/e | C,H,N |
|---|---|---|---|---|
| 90 | ![structure: -N(H)-C(=N-N=N-N)] | 235–237° | 423 (M$^+$) | XXX* |
| 100 | —HN—CH(CO$_2$Et)CH$_2$SH | | 487 (M$^+$) | XXX** |
| 101 | —HN—CH(CO$_2$Et)CH$_2$SCH$_3$ | 93–96° | 501 (M$^+$) | XXX |

*½ Hydrate
**½ Hydrate

EXAMPLE 19

Compounds or Table 4

Following the procedure of Example 17 but substituting the acid for 12 and allowing the resulting acid chloride to react with NH$_4$OH and diethylamine, respectively gave the amides of Table 4.

TABLE 4

| Compound Number | —NR$_6$R$_7$ | Melting point | Mass spectrum m/e | C,H,N |
|---|---|---|---|---|
| 38 | —NH$_2$ | 125–127° | 423 (M$^+$) | XXX |
| 39 | —NEt$_2$* | oil | 479 (M$^+$) | XXX |

*Et = ethyl.

EXAMPLE 20

3-(3-Acetoxypropyl)-5-(4-chlorophenyl)-1-phenyl-pyrazole (7)

Compound 1 (1.00 g, 3.20 mM), acetic anhydride (1.0 ml, 11 mM), pyridine (1.0 ml, 12 mM) and CH$_2$Cl$_2$ (30 ml) were admixed and the admixture so formed was stirred overnight at room temperature, poured into H$_2$O (150 ml) and extracted with CH$_2$Cl$_2$ (25 ml). The extracts were dried (Na$_2$SO$_4$), filtered and concentrated to an oil (1.1 g). Chromatography (silica gel 60; 70–230 mesh, 150 g) and elution with Et$_2$O afforded 1.10 g (94%) of 7 as a colorless oil.

NMR (CDCl$_3$) 2.05 (s, 3H, CH$_3$CO), 1.8–2.4 (m, 2H, —CH$_2$CH$_2$), 2.8 (dist t, J≃8 Hz, CH$_2$—), 4.2 (t, 2H, J=6, CH$_2$O), 6.32 (s, 1H, C$_4$—H), 7.1–7.5 (m, 9H, aromatic);
IR (neat) 2960, 1740, 1600; MS, m/e 354 (M$^+$), 311, 281, 268 (100%).

Anal. Calcd. for C$_{20}$H$_{19}$ClN$_2$O$_2$:C,67.69;H,5.40;N,7.89.
Found:C,67.78;H,5.36;N,8.07.

EXAMPLE 21

3-[5-(4-Chlorophenyl)-1-(4-methoxyphenyl)-3-pyrazolyl] propyl methyl ether (24)

To a suspension of NaH (0.135 g of 60% oil suspension, 3.37 mM) in THF (10 ml) at +5° C. was added a solution of 2 (1.05 g, 3.06 mM) in THF (20 ml). After stirring for 30 minutes, methyl iodide (MeI) (0.21 ml, 3.37 mM) was added and the reaction mixture was left to stir overnight. After quenching with CH$_3$OH, the reaction mixture was concentrated in vacuo, the residue was taken up in EtOAc, washed with H$_2$O, dried (Na$_2$SO$_4$), filtered, and concentrated in vacuo. Chromatography (40 g, Baker silica gel) with Et$_2$O as eluent afforded 24 (0.98 g, 90%) as a clear yellow oil.

NMR (CDCl$_3$) 1.8–2.4 (m, 2H, —CH$_2$CH$_2$C-H$_2$OCH$_3$), 2.6–3.0 (m, 2H, —CH$_2$CH$_2$CH$_2$OCH$_3$), 3.35 (s, 3H, —CH$_2$OCH$_3$), 3.48 (t, J=7 Hz, 2H, —CH$_2$C-H$_2$OCH$_3$), 3.78 (s, 3H, aromatic —OCH$_3$), 6.28 (s, 1H, C$_4$—H), 6.7–7.4 (m, 8H, aromatic); IR (neat) 1250, 830; MS, m/e 357 (M+1, 100%), 323 298.

Anal. Calcd. for C$_{20}$H$_{21}$ClN$_2$O$_2$:C,67.31;H,5.93;N,7.85.
Found:C,67.15;H,6.07;N,7.77.

EXAMPLE 22

5-(4-Chlorophenyl)-3-(3-hydroxybutyl)-1-(4-methoxyphenyl) pyrazole (20)

To a solution of methyl magnesium bromide (MeMgBr) (2.20 ml, 7.04 mM) in Et$_2$O (15 ml) at 0° C. was added a solution of the aldehyde 11 (1.60 g, 4.69 mM)in Et$_2$O (70 ml) dropwise over a 30 minute period. After stirring for 1 hour the reaction was quenched with a saturated, aqueous NH$_4$Cl solution. The reaction mixture was partitioned between EtOAc and H$_2$O. The EtOAc solution was dried (MgSO$_4$), filtered, and concentrated in vacuo. Chromatography (65 g, Baker 40 gm silica gel) of the residue with Et$_2$O as eluent afforded 20 (1.33 g, 79%) as a clear light yellow oil.

NMR (CDCl$_3$) 1.25 (d, J=6 Hz, 3H, —CH(OH)—CH$_3$) 1.6–2.2 (m, 2H, —CH$_2$—CH(OH)—), 2.2–2.8 (m, 1$\overline{\text{H}}$, —OH), 2.83 (t, J=7 Hz, 2H, CH$_2$), 3.78 (s, 3H, —OCH$_3$), 3.7–4.2 (m, 1H, —CH$_2$—C$\overline{\text{H}}$(OH)—CH$_3$), 6.27 (s, 1H, C$_4$—H), 6.7–7.4 (m, 8$\overline{\text{H}}$, aromatic); IR (neat) 3380; MS, m/e 356 (M+), 341, 312, 311, 298 (100%).

Anal. Calcd. for C$_{20}$H$_{21}$ClN$_2$O$_2$:C,67.31;H,5.93;N,7.85. Found:C,67.38;H,6.35;N,7.61.

EXAMPLE 23

5-(4-Chlorophenyl)-1-(4-methoxyphenyl)-3-(3-oxobutyl)pyrazole (23)

To a suspension of pyridinium chlorochromate (3.65 g, 16.93 mM) in CH$_2$Cl$_2$ (20 ml) was added the alcohol 20, (3.02 g, 8.46 mM) in CH$_2$Cl$_2$ (15 ml). After stirring for 4 hours, the reaction solution was decanted from the chromium precipitates that were washed with EtOAc (2×150 ml). The reaction solution and the washes were combined, filtered through florisil, and concentrated in vacuo. Chromatography (120 g, Baker 40 gm silica gel) with Et$_2$O:hexane (1:1 to 100% Et$_2$O) as eluent, followed by crystallization from Et$_2$O:hexane afforded 23, (2.09 g, 70%) as a white crystalline solid, mp=85°–86° C.

NMR (CDCl$_3$) 2.20 (s, 3H, —CO—CH$_3$), 2.7–3.2 (m, 4H, —CH$_2$CH$_2$—), 3.78 (s, 3H, —OCH$_3$), 6.25 (s, 1H, C$_4$—H), 6.7–7.4 (m, 8H, aromatic); IR (KBr) 1715; MS, m/e 355 (M+1), 321, 311.

Anal Calcd. for C$_{20}$H$_{19}$ClN$_2$O$_2$:C,67.70;H,5.40;N,7.90. Found:C,67.41;H,5.24;N,7.90.

EXAMPLE 24

5-(4-Chlorophenyl)-3-(3-hydroxy-3-methylbutyl)-1-(4-methoxyphenyl) pyrazole (27)

To a solution of MeMgBr (1.32 ml of 3.2M, 4.23 mM) in THF (15 ml) at 0° C., was added a solution of the ketone 23, (1.00 g, 2.82 mM) in THF (25 ml) dropwise over a 20 minute period. After stirring for 1 hour, the reaction mixture was quenched with a saturated NH$_4$Cl solution, diluted to a 100 ml volume with Et$_2$O, washed with H$_2$O, dried (Na$_2$SO$_4$), filtered, and concentrated in vacuo. Chromatography of the residue (Baker silica gel, 45 g) with Et$_2$O as eluent, afforded 27, (0.68 g, 80% corrected for recovered starting material) as a colorless oil.

NMR (CDCl$_3$) 1.30 (s, 6H, —C(CH$_3$)$_2$OH), 1.7–2.2 (m, 2H, CH$_2$C—OH), 2.2–2.7 (broad s, 1H, —OH), 2.7–3.1 (m, 2H, CH$_2$), 3.78 (s, 3H, —OCH$_3$), 6.25 (s, 1H, C$_4$—H), 6.6–7.4 (m, 8H, aromatic); IR (neat) 3390, 1250; MS (20 eV EI), m/e 370 (M+), 355, 312 (100%), 311, 298.

Anal. Calcd. for C$_{21}$H$_{23}$ClN$_2$O$_2$:C,68.01;H,6.25;N,7.55. Found:C,67.80;H,6.30;N,7.24.

EXAMPLE 25

5-(4-Chlorophenyl)-3-(3-oximinopropyl)-1-(4-methoxyphenyl) pyrazole (26)

To a solution of the aldehyde 11 (1.00 g, 2.93 mM) in EtOH (30 ml) was added hydroxylamine hydrochloride (0.31 g, 4.40 mM) and pyridine (0.47 g, 5.87 mM). After stirring overnight at room temperature, the reaction mixture was concentrated in vacuo. The remaining residue was taken up in CH$_2$Cl$_2$, washed with H$_2$O, dried (Na$_2$SO$_4$), filtered, and concentrated in vacuo. Crystallization from Et$_2$O:hexane afforded 26, (0.67 g, 64%) as a white crystalline solid, mp=134°–135° C.

NMR (CDCl$_3$) 2.5–3.3 (m, 5H, —CH$_2$CH$_2$— and =N—OH), 3.78 (s, 3H, —OCH$_3$), 6.30 (s, 1H, C$_4$—H), 6.5–7.4 (m, 9H, aromatic and —CH$_2$—CH=N—OH); IR (KBr) 3210; MS (20 eV EI), m/e 355 (M+), 338 (100%), 311, 297.

Anal. Calcd. for C$_{19}$H$_{18}$ClN$_3$O$_2$:C,64.13;H,5.10;N,11.81. Found:C,63.79;H,4.93;N,11.53.

EXAMPLE 26

5-(4-Chlorophenyl)-1-(4-methoxyphenyl)-3-[3(Z)-hexadecenyl]pyrazole (33)

To a solution of hexamethyldisilazane (0.70 ml, 3.34 mM) in THF (30 ml) at +5° C. was added 1.55M n-BuLi (1.97 ml, 3.05 mM). The cooling bath was removed and after 15 minutes tridecyltriphenyl phosphonium bromide (1.68 g, 3.20 mM) was added. After stirring for 0.5 hour, the aldehyde 11 (0.99 g, 2.90 mM) was added, the reaction mixture was stirred for an additional 30 minutes, and concentrated in vacuo. The residue was taken up in Et$_2$O:hexane (1:1), filtered, and concentrated in vacuo to afford crude 33 (1.42 g). Chromatography (Baker silica gel, 55 g) with Et$_2$O:hexane (1:2) as eluent afforded 33, (0.95 g, 65%) as a clear colorless oil.

NMR (CDCl$_3$) 0.7–3.1 (m, 29H, —CH$_2$CH$_2$CH=CH(CH$_2$)$_{11}$CH$_3$), 3.80 (s, 3H, —OCH$_3$), 5.3–5.7 (m, 2H, —CH=CH—), 6.30 (s, 1H, C$_4$—H), 6.6–7.5 (m, 8H, aromatic); IR (neat) 2940, 2860; MS (20 eV EI), 508 (M+2), 506 (M+), 449, 351, 338, 298 (100%).

Anal. Calcd. for C$_{32}$H$_{43}$ClN$_2$O:C,75.78;H,8.55;N,5.52. Found:C,75.54;H,9.03;N,5.44.

EXAMPLE 27

5-(4-Chlorophenyl)-1-(4-methoxyphenyl)-3-[4-phenyl-3(E)-butenyl] pyrazole (14); and
5-(4-chlorophenyl)-1-(4-methoxyphenyl)-3-[4-phenyl-3(E,Z)-butenyl] pyrazole (15)

To a suspension of pyridinium chlorochromate (6.29 g, 29.2 mM) in CH$_2$Cl$_2$ (40 ml) was added the alcohol 2, (5.00 g, 14.6 mM) in CH$_2$Cl$_2$ (30 ml). After stirring for 4 hours, the reaction solution was decanted from the chromium residue on the sides of the reaction vessel. This residue was washed with EtOAc (2×200 ml), and the washes were combined with the reaction solution, filtered through florisil, and concentrated in vacuo. Crystallization from Et$_2$O afforded the crude aldehyde 11 (4.20 g, 84%) contaminated with the dimer ester 16.

To a solution of hexamethyldisilazane (1.07 ml, 5.06 mM) in dry THF (50 ml) at +10° C. was added n-BuLi (2.98 ml, 4.62 mM). The cooling bath was removed, and after 15 minutes benzyltriphenyl phosphonium chloride (1.88 g, 4.84 mM) was added. After 45 minutes the crude aldehyde 11 (1.50 g, 4.40 mM) in THF (10 ml) was added, the reaction mixture was stirred for an additional 30 minutes and concentrated in vacuo. The residue was taken up into Et$_2$O (150 ml), filtered, and concentrated in vacuo.

Chromatography of this residue (Baker silica gel, 85 g) with Et$_2$O:hexane (1:1 to 100% Et$_2$O) afforded the E olefin 14, the E/Z olefins 15, and dimer ester 16. Compound 14 was crystallized from Et$_2$O:hexane. All products were combined with those of an equivalent run using the same procedure on a 2.93 mM scale of the aldehyde 11. This afforded the E olefin 14, (1.33 g, 44%) as a white crystalline solid, mp=93°–95° C., the mixed E/Z olefin 15, 7:3 Z:E (1.12 g, 37%) as a clear colorless oil; and dimer ester 16 (0.40 g, 8.0%).

Compound 14 NMR (CDCl$_3$) 2.4–3.2 (m, 4H, —CH$_2$CH$_2$—), 3.80 (s, 3H, OCH$_3$), 6.2–6.7 (m, 2H, CH=CH), 6.30 (s, 1H, C$_4$—H), 6.7–7.6 (m, 13H, aromatic); IR (KBr) 1245; MS, m/e 414 (M$^+$), 310, 297 (100%).

Anal. Calcd. for C$_{26}$H$_{23}$ClN$_2$O:C,75.26;H,5.59;N,6.75. Found:C,75.45;H,5.77;N,6.77.

Compound 15, NMR (CDCl$_3$) 2.5–3.2 (m, 4H, —CH$_2$CH$_2$—), 3.80 (s, 3H, OCH$_3$), 5.5–6.7 (m, 2H, —CH=CH—), 6.30 (s, 1H, C$_4$—H), 6.7–7.6 (m, 13H, aromatic); IR (neat) 1250; MS, m/e 414 (M$^+$), 311, 297 (100%).

Anal. Calcd. for C$_{26}$H$_{23}$ClN$_2$O:C,75.26;H,5.59;N,6.75. Found:C,74.86;H,5.96;N,6.61.

EXAMPLE 28

3-[5-(4-Chlorophenyl)-1-(4-methoxyphenyl)-3-pyrazolyl] propyl 3-[5-(4-Chlorophenyl)-1-(4-methoxyphenyl)-3-pyrazolyl] propionate (16)

To a solution of the carboxylic acid 12 (0.40 g, 1.12 mM) in THF (10 ml) at 0° C., was added one drop of DMF and oxalyl chloride (0.12 ml, 1.35 mM). After stirring for 15 minutes the cooling bath was removed and stirring was continued for 1 hour. The reaction mixture was concentrated in vacuo (to remove the excess oxalyl chloride), taken up in THF (10 ml), and cooled to 0° C. To this solution was added the alcohol 2 (0.38 ml, 1.12 mM) and Et$_3$N (0.47 ml, 3.36 mM). After 15 minutes the cooling bath was removed and stirring was continued for 1 hour. The reaction mixture was diluted to 50 ml with Et$_2$O, washed with H$_2$O, dried (MgSO$_4$), filtered and concentrated in vacuo. Chromatography (Baker silica gel, 45 g) with Et$_2$O:hexane (9:1) as eluent, afforded 16 (59%) as a white semisolid.

NMR (CDCl$_3$) 1.8–2.4 (m, 2H, —CH$_2$CH$_2$CH$_2$—), 2.5–3.3 (m, 6H, —CH$_2$—CH$_2$CH$_2$OCOCH$_2$CH$_2$—), 3.80 (s, 6H, 2-OCH$_3$), 4.25 (t, J=6.5 Hz, 2H, —CH$_2$CH$_2$OCO—), 6.27+6.33 (2s, 2H, 2×C$_4$—H), 6.7–7.5 (m, 16H, aromatic); IR (KBr) 1730; MS (DCI), 681 (M+1), 325.

Anal. Calcd. for C$_{38}$H$_{34}$Cl$_2$N$_4$O$_4$:C,66.96;H,5.03;N,8.22. Found:C,66.60;H,4.90;N,7.83.

EXAMPLE 29

3-[4-(4-Carbomethoxyphenyl)-3(E)-butenyl]-5-(4-chlorophenyl)-1-(4-methoxyphenyl) pyrazole (25)

To a solution of hexamethyldisilazane (1.08 ml, 5.13 mM) in THF (50 ml) at +5° C. was added n-BuLi (3.02 ml of 1.55M, 4.68 mM). After 15 minutes (4-carbomethoxyphenyl)triphenyl phosphonium chloride (2.19 g, 4.91 mM) was added, and the cooling bath was removed. After 30 minutes the aldehyde 11 (1.52 g, 4.46 mM) in THF (10 ml) was added, and the reaction mixture was stirred for an additional 0.5 hour. Concentration in vacuo of the reaction mixture and chromatography (Baker silica gel, 80 g) with Et$_2$O:hexane (1:1 to 100% Et$_2$O) as eluent afforded 25. Recrystallization from Et$_2$O afforded pure 25 (1.10 g, 48%) as a white crystalline solid, mp=126°–128° C.

NMR (CDCl$_3$) 2.5–3.1 (m, 4H, —CH$_2$CH$_2$—), 3.80 (s, 3H, —OCH$_3$), 3.90 (s, 3H, —COOCH$_3$), 5.8–6.7 (m, 2H, —CH=CH—), 6.30 (s, 1H, C$_4$—H), 6.7–8.2 (m, 12H, aromatic); IR (KBr) 1725; MS, m/e 472 (M$^+$), 441, 297 (100%).

Anal. Calcd. for C$_{28}$H$_{25}$ClN$_2$O$_3$:C,71.10;H,5.33;N,5.92. Found:C,71.30;H,5.22;N,5.97.

EXAMPLE 30

Methyl 3-[5-(4-chlorophenyl)-1-(4-methoxyphenyl)-3-pyrazolyl] propionate (19)

To a solution of the acid 12 (0.98 g, 2.75 mM) in Et$_2$O (10 ml) and CH$_2$Cl$_2$ (15 ml) at 0° C., was added a CH$_2$N$_2$ solution in Et$_2$O (prepared from N-nitroso-N-methylurea, 40% KOH/Et$_2$O) until a persistent yellow color was observed in the reaction mixture. The reaction mixture was dried (MgSO$_4$), filtered and concentrated in vacuo. Crystallization from EtOAc:hexane afforded 19 (0.85 g, 83%) as a white crystalline solid, mp =117°–118° C.

NMR (CDCl$_3$) 2.5–3.4 (m, 4H, —CH$_2$CH$_2$—), 3.70 (s, 3H, —COOCH$_3$), 3.80 (s, 3H, —OCH$_3$), 6.28 (s, 1H, C$_4$—H), 6.7–7.4 (m, 8H, aromatics). IR (KBr) 1730; MS, m/e 370 (M$^+$), 339, 311 (100%).

Anal. Calcd. for C$_{20}$H$_{19}$ClN$_2$O$_3$:C,64.77;H,5.16;N,7.56. Found:C,64.47;H,5.15;N,7.65.

EXAMPLE 31

3-(3-Acetoacetoxypropyl)-5-(4-chlorophenyl)-1-(4-methoxyphenyl) pyrazole (59)

5-(4-Chlorophenyl)-3-(3-hydroxypropyl)-1-(4-methoxyphenyl) pyrazole (1.71 g, 0.005 moles) and 2,2,6-trimethyl-1,3-dioxen-4-one (0.71 g, 0.005 moles) were dissolved in 100 ml of xylenes. The solution was stirred under reflux for 16 hours. At that time, the solution was cooled to room temperature, and concentrated in vacuo to a yellow oil. The oil was flash chromatographed on silica gel to afford 59 (1.7 g, 80%) as a pale yellow oil.

NMR (CDCl$_3$) 1.8–2.4 (m, 2H, CH$_2$CH$_2$CH$_2$), 2.1 (s, 3H, COCH$_3$), 2.8 (t, 2H, J=7 Hz, CH$_2$), 3.48 (s, 2H, COCH$_2$CO), 3.85 (s, 3H, OCH$_3$), 4.25 (t, 2H, J=7 Hz, CH$_2$OCO), 6.25 (s, 1H, C$_4$—H), 6.9 (d, J=8 Hz, 2 aromatic H), 7.0–7.4 (m, 6H, aromatic H); IR (neat) 1750, 1725; MS, m/e 426 (M$^+$), 341.

Anal. Calcd. for C$_{23}$H$_{23}$ClN$_2$O$_4$:C,64.71;H,5.43;N,6.56. Found:C,64.97;H,5.67;N,6.13.

EXAMPLE 32

3-[5-(4-Chlorophenyl)-1-(4-methoxyphenyl)-3-pyrazolyl]propylamine (96)

To a suspension of LiAlH$_4$ (0.13 g, 3.5 mM) in THF (15 mL) was added a solution of the amide 31, (1.00 g, 2.81 mM) in THF (15 ml), dropwise, keeping the reaction temperature below reflux. The reaction mixture was heated to reflux, and refluxed for 17 hours, when it was quenched with 0.13 ml H$_2$O, 0.13 mL 20% NaOH solution and an additional 0.39 ml H$_2$O. The reaction mixture was filtered and concentrated in vacuo. The remaining residue was taken up into EtOAc (50 mL)

and extracted with a 1.0N HCl solution (2×25 mL). The aqueous extracts were combined and washed with EtOAc (25 mL), neutralized with a 2N NaOH solution, and extracted with EtOAc (2×50 mL). The organic extracts were dried ($Na_2SO_4$), filtered and concentrated in vacuo to afford the title compound (0.86 g, 90%) as a light yellow oil.

NMR ($CDCl_3$) 1.6–2.3 (m, 4H, —$CH_2$$\underline{CH_2}$$CH_2NH_2$), 2.6–3.1 (m, 4H, —$\underline{CH_2}$$CH_2$$\underline{CH_2}$$NH_2$), 3.78 (s, 3H, —$OCH_3$), 6.27 (s, 1H, $C_4$—H), 6.6–7.5 (m, 8H, aromatic); IR (neat) 3380, 1520; MS (DCI), m/e 344 ($MH^+$ +2), 342 ($MH^+$, 100%).

Anal. Calcd. for $C_{19}H_{20}ClN_3O$: C,66.76;H,5.90;N,12.29. Found:C,66.70;H,5.97;N,11.83.

EXAMPLE 33

3-[5-(4-Chlorophenyl)-1-(4-methoxyphenyl)-3-pyrazolyl]propanenitrile (95)

To a suspension of compound 31, (7.75 g, 21.8 mM) in dry benzene (400 mL) was added $SOCl_2$ (4.78 mL, 65 mM). The reaction mixture was heated to reflux for three days and then cooled to 0° C. Any excess $SOCl_2$ was decomposed with ice water. 50 mL of $H_2O$ was added to the reaction mixture which was then neutralized with 50% NaOH, washed with $H_2O$ (2×50 mL), dried ($Na_2SO_4$), filtered, and concentrated in vacuo. Crystallization from $Et_2O$, Hexane afforded the title compound (6.43 g, 87%) as a light yellow crystalline solid, mP=107°–109° C.

NMR ($CDCl_3$) 2.4=3.2 (m, 4H, —$CH_2CH_2$—), 3.82 (s, 3H, $OCH_3$), 6.41 (s, 1H, $C_4$—H), 6.7–7.5 (m, 8H, aromatic); IR (KBr) 2250, 1510; MS(EI) m/e 339 (M+2, 1Cl), 337 ($M^+$, 100%).

Anal. Calcd. for $C_{19}H_{16}ClN_3O$:C,67.55;H,4.77;N,12.44. Found:C,67.23;H,4.88;N,12.21.

EXAMPLE 34

3-[5-(4-Chlorophenyl)-1-(4-methoxyphenyl)-3-pyrazolyl]-N-methyl-N-succinyloxy- propanamide. (129)

To a solution of the hydroxamic acid 3 (5.0 g, 12.96 mM) in dry pyridine (13 ml) was added succinic anhydride (1.3 g, 12.99 mM) in pyridine (5 ml) and the resulting solution was stirred for 72 hours. The pyridine was removed in vacuo and the residue was triturated with hexane and recrystallized from $Et_2O$ to afford pure 34 (6.21 g, 98%) as a white solid, mp=146°–147°. MS, m/e 485($M^+$).

Anal. Calcd. for $C_{24}H_{24}ClN_3O_6$: C,59.32; H,4.98; N,8.65. Found: C,59.68; H,4.97; N,8.75.

Employing a similar procedure, the compounds of Table 5 were synthesized.

TABLE 5

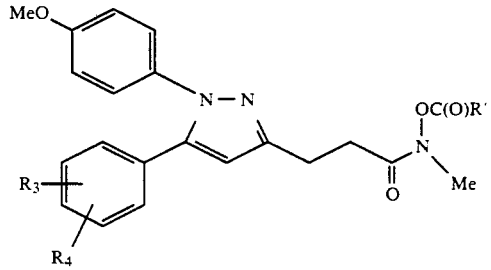

| Compound Number | R3,R4 | R' | Melting Point | Mass Spectrum (m/e) | C,H,N |
|---|---|---|---|---|---|
| 130 | 4-Me | $CH_2CH_2CO_2H$ | 131–132° | 465 ($M^+$) | XXX |
| 131 | 3,4-di-Me | $CH_2CH_2CO_2H$ | 124–125° | 479 ($M^+$) | XXX |
| 132 | 4-Cl | $CH_2CH_2CH_2CO_2H$ | glass | 385 (M-114) | XXX |
| 133* | 4-Cl | $CH_2CH_2CO_2Na$ | 240° (dec) | 507 ($M^+$) | XXX |

*Prepared as the sesquihydrate by treatment of compound prepared in Example 34 with 1N NaOH

EXAMPLE 35

3-[5-(4-Chlorophenyl)-1-(4-methoxyphenyl)-3-pyrazolyl]-N',N'-dimethylglycinyloxy-N-methyl-propanamide (134)

Compound 3 (6.0 g, 15.55 mM) was added to a suspension of N,N-dimethyl-glycine (1.61 g, 15.61 mM) and N',N'-dicyclohexylcarbodiimide (3.21 g, 15.55 mM) in dry pyridine (22 ml) under nitrogen and stirred for 44 hours. The solvent was removed in vacuo and the residue triturated with $CH_2Cl_2$, filtered, and the filtrate evaporated to dryness. Recrystallization from $CH_2Cl_2/Et_2O$ afforded pure 35 (6.8 g, 93%) as a white solid, mp=103°–104°, MS, m/e 470 ($M^+$).

Anal. Calcd. for $C_{24}H_{27}ClN_4O_4$: C,61.20; H,5.78; N,11.90. Found: C,61.26; H,5.94; N,11.79.

The oxalate salt of 35 was synthesized as the trihydrate as a white solid, mp=114°–115°.

Anal.Calcd.for $C_{24}H_{27}ClN_4O_4.C_2H_2O_4.3H_2O$: C,50.77;H,5.74;N,9.11. Found:C,50.68;H,5.73;N,8.64.

In a similar manner, the compounds of Table 6 were synthesized.

TABLE 6

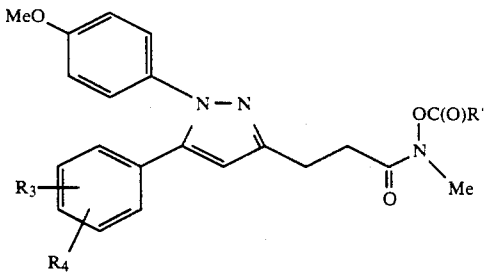

| Compound Number | R3,R4 | R' | Melting Point | Mass Spectrum (m/e) | C,H,N |
|---|---|---|---|---|---|
| 135 | 4-Cl | c-C5H9NHCO2-t-Bu | 155–156° | 596 (M+) | XXX |
| 136 | 4-Cl | CH2CH2COMorpholine | 108–109° | 554 (M+) | XXX |
| 137 | 4-Cl | CH2CH2CONEt2 | 43–44° | 540 (M+) | XXX* |
| 138 | 4-Me | CH2NMe2 | 77–78° | 450 (M+) | XXX |

*¼ hydrate

EXAMPLE 36

3-[5-(4-Chlorophenyl)-1-(4-methoxyphenyl)-3-pyrazolyl]N-chloroacetyloxy-N-methylpropanamide (139)

To a solution of 3 (7.0 g, 18.14 mM) in anhydrous THF (125 ml) was added methylmorpholine (1.99 ml, 18.1 mM) and the resulting solution was cooled to −10° C. under nitrogen. Chloroacetyl chloride (1.44 ml, 18.1 mM) was added and stirred for 10 minutes, filtered and the filtrate concentrated in vacuo. The residue was recrystallized from Et2O to afford pure 36 (5.7 g, 68%) as a white solid, mp=110°–111°. MS, m/e 461 (M+).

Anal. Calcd. for C22H21Cl2N3O4: C,57.15; H,4.58; N,9.09. Found: C,57.42; H,4.55; N,8.99.

Employing a similar procedure to that of Example 36, the compounds of Table 7 were synthesized.

TABLE 7

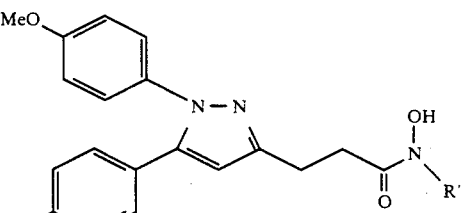

| Compound Number | R' | Melting Point | Mass Spectrum (m/e) | C,H,N |
|---|---|---|---|---|
| 140 | CH3 | 130–132° | 427(M+) | XXX |
| 141 | C(CH3)3 | 144–145° | 469(M+) | XXX |
| 142 | CH2OMe | 98–100° | 457(M+) | XXX* |

*¼ hydrate

Following the procedure of Example 5, but using the appropriate hydroxylamine gave the compounds of Table 8.

TABLE 8

| Compound Number | R' | Melting Point | Mass Spectrum (m/e) | C,H,N |
|---|---|---|---|---|
| 143 | CH2CH2Pyr | glass | 695(M+) | XXX* |
| 144 | CHMeCO2Et | 125–127° | 471(M+) | XXX |
| 145 | CHMeCO2H | 148–150° | 443(M+) | XXX |
| 146 | C8H17 | oil | 483(M+) | XXX |

*¼ hydrate

EXAMPLE 37

3-[4-Bromo-5-(4-Chlorophenyl)-1-(4-methoxyphenyl)-3-pyrazolyl]-propionic acid (147)

The acid 12 (3.57 g, 10 mM) and N-bromosuccinimide (1.78 g, 10 mM) were dissolved in a mixture of CCl4 (150 ml) and CHCl3 (20 ml) and allowed to stir for 16 hours. The solvents were evaporated in vacuo and the residue was dissolved in CHCl3, washed with H2O, dried (Na2SO4), filtered and evaporated to give an oil which was crystallized from Et2O to afford pure 37 (2.18 g, 50%) as a white solid, mp=147.5°–148°. MS, m/e 435 (MH+).

Anal. Calcd. for C19H16BrClN2O3:C,52.37; H,3.70; N,6.43. Found: C,52.58; H,3.69; N,6.27.

Substitution of N-chlorosuccinimide for N-bromosuccinimide gave the corresponding 4-chloro derivative as a white solid, mp=123.5°–124.5°. MS, m/e 91(MH+) (Compound No. 182).

Anal. Calcd. for C19H16Cl2N2O3.¼H2O: C,57.66; H,4.20; N,7.08. Found: C,57.78; H,4.12; N,6.96.

Using the acids synthesized in Example 37 and following the procedure described in Example 5 gave the compounds of Table 9.

TABLE 9

[Structure: pyrazole with MeO-phenyl on N, R3,R4-substituted phenyl, X substituent, and CH2CH2C(=O)N(R)OH side chain]

| Compound Number | X | R3,R4 | R | Melting Point | Mass Spectrum (m/e) | C,H,N |
|---|---|---|---|---|---|---|
| 148 | Br | 4-Cl | Me | foam | 463(M+) | XXX |
| 149 | Cl | 4-Cl | Me | foam | 419(M+) | XXX* |
| 150 | Br | 4-Cl | H | 150–151° | 449(M+) | XXX |

*hydrate

Substituting Compound 2 for the acid 12 in Example 37 afforded 4-bromo-5-(4-chlorophenyl)-3-(3-hydroxypropyl)-1-(4-methoxyphenyl)pyrazole (Compound No. 183), as an off-white solid, 87%, mp=118.5°–120°. MS, m/e 420 (M+).

Anal. Calcd. for $C_{19}H_{18}BrClN_2O_2$: C, 54.11; H, 4.30; N. 6.64. Found: C, 54.20; H, 4.35; N. 6.59.

Following a similar procedure, but employing N-chlorocuccinimide gave 4-chloro-5-(4-chlorophenyl)-3-(3-hydroxypropyl)-1-(4-methoxyphenyl)pyrazole as a tan solid; mp=113°–115°. MS, m/e 376 (M+).

Anal. Cald. for $C_{19}H_{18}Cl_2N_2O_2$: C, 60.49; H, 4.81; N, 7.43. Found: C, 60.30; H, 4.82; N, 7.36.

EXAMPLE 38

N-[3-[5-(4-Chlorophenyl)-1-(4-methoxyphenyl)-3-pyrazolyl]propyl]hydroxyl-amine (151)

To a solution of the oxime 26 (2.70 g, 7.59 mM) in MeOH (50 ml), containing methyl orange (2 mg) as as indicator, was added a solution of NaBH3CN (0.52 g, 8.4 mM) in MeOH (20 ml), and a solution of 2N HCl, simultaneously, at such a rate to maintain a pH of 3 to 4. The reaction was stirred for 3 hours at room temperature, acidified to pH 1 and concentrated in vacuo. The residue was diluted with H2O (100 ml), adjusted to pH 8.5 with 5N NaOH, and extracted with EtOAc. The extracts were combined, dried (Na2SO4), filtered and concentrated in vacuo. The residue was chromatographed on Merck Silica Gel 60 (90 g, 230–400 mesh) with EtOAc:MeOH (9:1) as eluent. Crystallization from Et2O afforded pure 38 (1.64 g, 60%) as a white solid, mp=91°–93°. MS, m/e 357(M+).

Anal. Calcd. for $C_{19}C_{20}ClN_3O_2$: C,63.77; H,5.63; N,11.74. Found: C,63.63; H,5.74; N,11.63.

EXAMPLE 39

N-[3-[5-(4-Chlorophenyl)-1-(4-methoxyphenyl)-3-pyrazolyl]propyl]-N-hydroxy-acetamide (152)

To a solution of hydroxylamine 38 (1.25 g, 3.49 mM) and Et3N (0.97 ml, 6.9 mM) in THF (35 ml) was added acetyl chloride (0.25 ml, 3.5 mM) and the reaction mixture stirred for 1 hour, diluted with EtOAc (165 ml), washed with H2O, dried (Na2SO4), filtered and concentrated in vacuo to give a residue which was recrystallized from EtOAc:Et2O to afford pure 39 (1.06 g, 76%) as a white crystalline solid, mp=121°–123°. MS, m/e 399 (M+).

Anal. Calcd. for $C_{21}H_{22}ClN_3O_3$: C,63.07; H,5.55; N,10.51. Found: C,62.83; H,5.95; N,10.43.

Following a similar procedure to that of Example 39 and employing the appropriate acyl chloride afforded the compounds of Table 10.

TABLE 10

[Structure: pyrazole with MeO-phenyl on N, 4-Cl-phenyl substituent, and CH2CH2CH2N(R)OH side chain]

| Compound Number | R | Melting Point | Mass Spectrum (m/e) | C,H,N |
|---|---|---|---|---|
| 153 | CO-t-Bu | 138–140° | 441(M+) | XXX |
| 154 | COC7H15 | 90–91° | 483(M+) | XXX |
| 155 | COPh | foam | 461(M+) | XXX |
| 156 | SO2CH3 | 173–175° | 435(M+) | XXX |

EXAMPLE 40

Ethyl N-[3-[5-(4-chlorophenyl)-1-(4-methoxyphenyl)-3-pyrazolyl]-propyl]- hydroxyoxamate (157)

Following a similar procedure to that of Example 39, but employing ethyl oxalyl chloride in place of acetyl chloride afforded 40 as a white foam; MS, m/e 457 (M+).

Anal. Calcd. for $C_{23}H_{24}ClN_3O_3$: C,60.33; H,5.28; N,9.18. Found: C,60.55; H,5.67; N,9.18.

EXAMPLE 41

N-[3-[5-(4-Chlorophenyl)-1-(4-methoxyphenyl)-3-pyrazolyl]propyl]-N,N'-dihydroxyoxamide (158)

To a solution of hydroxylamine.HCl (0.25 g, 3.5 mM) and the ester 7C (0.81 g, 1.8 mM) in EtOH (17 ml) was added a 1N NaOEt solution (7.1 ml, 7.1 mM). After stirring for 2.5 hours the reaction mixture was acidified and concentrated in vacuo. The residue was diluted with CHCl3, washed (H2O), dried (Na2SO4), filtered and concentrated in vacuo. Crystallization from EtOAc:Et2O afforded pure 41 as a white crystalline solid, mp=145°–146.5° MS, m/e 444 (M+).

Anal. Calcd. for $C_{21}H_{21}ClN_4O_5.0.25\ H_2O$: C,56.13;H,4.82;N,12.47. Found: C,56.16;H,4.76;N,12.32.

EXAMPLE 42

2-[5-(4-Chlorophenyl)-1-(4-methoxyphenyl)-3-pyrazolyl]-ethyl amine (159)

To a solution of the acid 12 (1.0 g, 2.8 mM) in benzene (25 ml) was added Et3N (0.39 ml, 2.8 mM) and diphenylphosphoryl azide (0.60 ml, 2.8 mM). After stirring overnight at room temperature, the reaction mixture was heated to 70° C. for 1.5 hours, cooled and concentrated in vacuo. Dioxane (2 ml), followed by a solution of concentrated HCl (0.3 ml) in dioxane (2 ml) was added, and the reaction mixture was heated to reflux for 2 hours, cooled and diluted to 50 ml with EtOAc. The organic solution was washed with a 0.25N NaOH solution, and extracted with 1N HCl. The extracts were combined, basified with 5N NaOH, and extracted with EtOAc, dried, filtered and concentrated in vacuo. Crystallization from Et$_2$O afforded pure 42 (0.62 g, 68%) as a light yellow crystalline solid, mp=95°-97°. MS, m/e 327 (M+).

Anal. Calcd. for $C_{18}H_{18}ClN_3O$: C, 65.95; H,5.53; N,12.82. Found: C, 66.14; H,5.57; N,13.10.

EXAMPLE 43

Ethyl 2-[5-(4-chlorophenyl)-1-(4-methoxyphenyl)-3-pyrazolyl]-ethylamine-N-oxoacetate (160)

To a solution of the amine 42 (3.24 g, 9.8 mM) and Et$_3$N (1.56 ml, 10.9 mM) in THF (100 ml) was added ethyloxalyl chloride (1.1 ml, 9.8 mM). After stirring overnight the reaction mixture was diluted to 400 ml with EtOAc, washed with H$_2$O, dried (Na$_2$SO$_4$), filtered and concentrated in vacuo. The residue was chromatographed on Merck Silica Gel 60 (110 g, 230-400 mesh) with EtOAc:Hexane (3:1) as eluent. Crystallization from EtOAc:Hexane afforded pure 43 (3.6 g, 85%) as a white crystalline solid, mp=93°-94°. MS, m/e 427 (M+).

Anal. Calcd. for $C_{22}H_{22}ClN_3O_4$: C,61.75; H,5.18; N,9.82. Found: C,61.56; H,5.29; N,9.78.

EXAMPLE 44

Ethyl 3-[5-(4-chlorophenyl)-1-(4-methoxyphenyl)-3-pyrazolyl]-propylamine-N-oxoacetate (161)

Following the procedure of Example 43, but substituting the amine 96 of Example 32 for the amine 42 afforded 44 as a yellow oil; MS, m/e 441 (M+).

Anal. Calcd. for $C_{23}H_{24}ClN_3O_4$: C,62.51; H, 5.49; N,9.51. Found: C, 62.41; H,5.66; N,9.35.

The compounds of Table 11 were synthesized from compounds 43 or 44 by standard methods.

TABLE 11

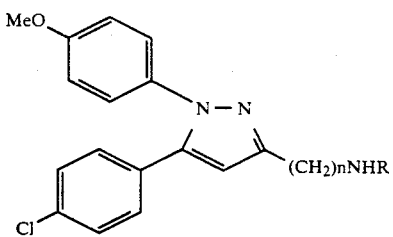

| Compound Number | n | R | Melting Point | Mass Spectrum (m/e) | C,H,N |
|---|---|---|---|---|---|
| 162 | 3 | COCON(Me)OH | 111-113° | 442(M+) | XXX |
| 163 | 2 | COCON(Me)OH | 110-111° | 428(M+) | XXX |
| 164 | 3 | COCONHOH | 183-185° | 428(M+) | XXX |
| 165 | 2 | COCONHOH | 188-189° | 414(M+) | XXX |
| 166 | 3 | COCO$_2$H | 157-159° | 413(M+) | XXX |

EXAMPLE 45

N-Acetyl-3-[5-(4-chlorophenyl)-1-(4-methoxyphenyl)-3-pyrazolyl]-propyl-amine (167)

To a solution of the amine 96 (0.96 g, 2.8 mM) and Et$_3$N (0.59 ml, 4.2 mM) in THF (25 ml) was added acetyl chloride (0.2 ml, 2.8 mM). After stirring for 1 hour the reaction mixture was diluted to 200 ml with EtOAc, washed with H$_2$O, dried, filtered and concentrated in vacuo. Crystallization from EtOAc:Et$_2$O afforded pure 45 (0.78 g, 72%) as an off-white crystalline solid, mp=129°-131°. MS, m/e 383 (M+).

Anal. Calcd. for $C_{21}H_{22}ClN_3O_2$: C,65.70; H,5.78; N,10.95. Found: C,65.85; H,6.00; N,10.88.

Following the procedure of Example 45, but substituting trimethylacetyl chloride, methanesulfonyl chloride and diethyl chlorophosphate respectively for acetyl chloride gave the compounds of Table 12.

TABLE 12

| Compound Number | R | Melting Point | Mass Spectrum (m/e) | C,H,N |
|---|---|---|---|---|
| 168 | CO-t-Bu | 104-105° | 425(M+) | XXX |
| 169 | SO$_2$Me | 108-110° | 419(M−) | XXX |
| 170 | PO(OEt)$_2$ | oil | 477(M−) | XXX* |

*¼ hydrate

EXAMPLE 46

N-Acetyl-3-[5-(4-chlorophenyl)-1-(4-methoxyphenyl)-3-pyrazolyl]-N-hydroxy-propanamide (171)

A white slurry of compound 29 of Example 12 (5.0 g, 13.45 mM) in CH$_2$Cl$_2$ (200 ml) and Et$_3$N (1.88 ml, 13.48 mM) was cooled to −10° C. under nitrogen, and treated with acetyl chloride (0.91 ml, 12.8 mM). The mixture was allowed to stir at −10° C. for 45 minutes, filtered and the filtrate concentrated in vacuo to give crude product which was purified via flash column chromatography (EtOAc) and recrystallized from Et$_2$O to afford 46 as a white solid, mp=110°-111°. MS, m/e 413 (M+).

Anal. Calcd. for $C_{21}H_{20}ClN_3O_4$: C,60.94; H,4.87; N,10.15. Found: C,61.19; H,5.15; N, 9.77.

EXAMPLE 47

N-Acetyl-N-acetoxy-[5-(4-chlorophenyl)-1-(4-methoxyphenyl)-3-pyrazolyl]-propanamide (172)

Following the procedure of Example 46, but employing 2 equivalents of acetyl chloride afforded 47 as a white solid, mp=111°-112°. MS, m/e 455 (M+).

Anal. Calcd. for $C_{23}H_{22}ClN_3O_5$: C,60.59; H,4.86; N,9.22. Found: C,60.52; H,5.12; N,9.06.

EXAMPLE 48

5-(4-Chlorophenyl)-1-(4-methoxyphenyl)-3-(3-oxobutyl)pyrazole thiazol-2-yl hydrazone (173)

A solution of compound 23 (2.15 g, 6.06 mM) in EtOH (6.2 ml) and glacialacetic acid (0.2 ml) was warmed to 35° and 2-thiazolylhydrazine (0.698 g, 6.06 mM) was added. Stirring was continued for 80 minutes and the resulting brown solution was cooled to room temperature for 1 hour, then allowed to stand at −15°, filtered, and recrystallized from EtOH to afford 48 as a tan solid (1.22 g, 45%), mp=128°-129°. MS, m/e 451 (M+).

Anal. Calcd. for $C_{23}H_{22}ClN_5S$: C,61.12; H,4.91; N,15.50. Found: C,60.89; H,4.81; N,15.12.

Following the procedure of Example 48, but substituting the appropriate ketone from Table 15 or aldehyde 11 for compound 23 afforded the compounds of Table 13.

TABLE 13

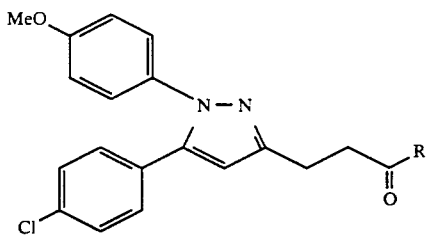

| Compound Number | R | Melting Point | Mass Spectrum (m/e) | C,H,N |
|---|---|---|---|---|
| 174 | H | 169-170° | 437(M+) | XXX |
| 175 | $CH_2CH_3$ | 149-152° | 465(M+) | XXX* |
| 176 | Phenyl | 104-105° | 513(M+) | XXX** |

*¼ hydrate
**½ hydrate

Following the procedure of Example 22, but substituting ethyl magnesium bromide, phenyl magnesium bromide and t-butyl magnesium chloride for methyl magnesium bromide gave the compounds of Table 14.

TABLE 14

| Compound Number | R | Melting Point | Mass Spectrum (m/e) | C,H,N |
|---|---|---|---|---|
| 177 | Et | 84-85° | 370(M+) | XXX |
| 178 | Ph | 107-108° | 418(M+) | XXX* |
| 179 | t-Bu | 127-129° | 398(M+) | XXX* |

*¼ hydrate

Following the procedure of Example 23, but substituting the appropriate alcohol from Table 14 for compound 20 afforded the compounds of Table 15.

TABLE 15

| Compound Number | R | Melting Point | Mass Spectrum (m/e) | C,H,N |
|---|---|---|---|---|
| 180 | Et | 89-90 | 368(M+) | XXX |
| 181 | Ph | 138-139° | 416(M+) | XXX |

EXAMPLE 49

2-[5-(4-Chlorophenyl)-1-(4-methoxyphenyl)-3-pyrazolyl]-ethyl carboxamidoxime (184)

To a suspension of nitrile 95 (1.0 g, 2.96 mM) in MeOH (6 ml) was added $NaHCO_3$ (0.50 g, 5.9 mM) and a solution of hydroxylamine.HCl (0.40 g, 5.9 mM) in $H_2O$ (5 ml). The reaction was heated to reflux for 16 hours, concentrated in vacuo and the residue partitioned between $H_2O$ and $CHCl_3$. The $CHCl_3$ layer was dried ($Na_2SO_4$), filtered and concentrated in vacuo to a white foam. Crystallization from EtOAc afforded pure 49 (0.65 g, 59%) as a white crystalline solid, mp=132°-134°. MS, m/e 370 (M+).

Anal. Calcd. for $C_{19}H_{19}ClN_4O_2.0.25$ $H_2O$: C,60.80;H,5.24;N,14.9. Found: C,60.73;H,5.18;N,14.74.

EXAMPLE 50

N-Hydroxy-N-methyl-2-[5-(4-chlorophenyl)-1-(4-methoxyphenyl)-3-pyrazolyl]ethylcarboximidamide Monohydrate (185)

Following the procedure of Example of 48, but substituting N-methylhydroxylamine.HCl for hydroxylamine.HCl afforded 50 as a white solid, mp=106°-110°. MS, m/e 384 (M+).

Anal. Calcd. for $C_{20}H_{21}N_4O_2.H_2O$: C,59.62;H,5.75;N,13.91. Found: C,59.62;H,5.65;N,13.61.

Following the procedure of Example 18, but substituting octylamine for diethylamine gave the following compound.

| Compound Number | $NR_6R_7$ | Melting Point | Mass Spectrum (m/e) | C,H,N |
|---|---|---|---|---|
| 186 | $NHC_8H_{17}$ | 95-96° | 467(M+) | XXX |

EXAMPLE 51

3-[1-(4-Methoxyphenyl)-5-(4-methylphenyl)-4-methyl-3-pyrazolyl]-N-hydroxy-N-methylpropanamide (187)

5-Methyl-6-(4-methylphenyl)-4,6-dioxohexanoic acid

Following the procedure employed for the synthesis of the 4,6-dioxohexanoic acids of Table 2″-AP, but substituting 4′-methylpropiophenone for the appropriately substituted acetophenone gave the title compound 5-methyl-6-(4-methylphenyl)-4,6-dioxohexanoic acid.

3-[1-(4-Methoxyphenyl)-5-(4-methylphenyl)-4-methyl-3-pyrazolyl]propionic acid

Following the procedure employed for the synthesis of the pyrazole propionic acids of Table 2", but substituting compound 5-methyl-6-(4-methylphenyl)-4,6-dioxohexanoic acid for the appropriate 6-aryl-4,6-diketohexanoic acid gave 3-[1-(4-methoxyphenyl)-5-(4-methylphenyl)-4-methyl-3-pyrazolyl]propionic acid.

3-[1-(4-Methoxyphenyl)-5-(4-methylphenyl)-4-methyl-3-pyrazolyl]-N-hydroxy-N-methylpropanamide Following the procedure of Example 5, but substituting the propionic acid compound obtained above for the acid 12 gave 3-[1-(4-methoxyphenyl)-5-(4-methylphenyl)-4-methyl-3-pyrazolyl]-N-hydroxy-N-methylpropanamide the title compound.

IN VIVO ALLEVIATION OF INFLAMMATION

Polyarthritis was induced in Lewis strain laboratory rats (weight=about 200 grams) by injection of a suspension of *Mycobacterium butyricum* in mineral oil into the subplantar tissue of the mammal's hind paws. On day 10 after the injection, the rats were assigned to groups, and paw volumes and body weights were recorded. Paw volumes of the contralateral, uninjected hind paw were determined by mercury plethylsmography. Per oral (p.o.) dosing began and continued for five consecutive days thereafter. On day 14 after the initial injection, approximately four hours after the final dose was administered, paw volumes and body weights were recorded and quantitated.

Anti-inflammatory activity of the substituted pyrazole compounds is expressed as the percent inhibition of paw volume increase. The results of this study for several compounds of the structure shown below are shown in Table 16, hereinafter.

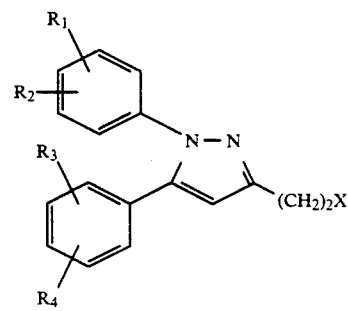

TABLE 16

| | | | In Vivo Alleviation of Inflammation in Rats[1] | |
|---|---|---|---|---|
| No. | $R_1, R_2$[2] | $R_3, R_4$[3] | X | % INH. p.o.* (mpk) |
| 1 | H | 4-Cl | —CH$_2$OH | 62% at 50 |
| 2 | 4-OMe | 4-Cl | —CH$_2$OH | [ED$_{50}$ = 3.6] |
| 3 | 4-OMe | 4-Cl | —CON(CH$_3$)OH | [ED$_{50}$ = 4.1] |
| 4 | 4-Cl | 4-Cl | —CH$_2$OH | 68% at 50 |
| 7 | H | 4-Cl | —CH$_2$OAc | 54% at 50 |
| 8 | 3,4-diCl | 4-Cl | —CH$_2$OH | 41% at 50 |
| 10 | 4-OMe | H | —CH$_2$OH | 30% at 50 |
| 11 | 4-OMe | 4-Cl | —CHO | [ED$_{50}$ = 2.6] |
| 12 | 4-OMe | 4-Cl | —CO$_2$H | [ED$_{50}$ = 5.2] |
| 13 | 4-OMe | 4-Cl | —CO$_2$Na | [ED$_{50}$ = 1.8] |
| 16 | 4-OMe | 4-Cl | —CO$_2$(CH$_2$)$_3$pyrazole | 82% at 25 |
| 17 | H | 4-Cl | —CO$_2$H | 50% at 25 |
| 19 | 4-OMe | 4-Cl | —CO$_2$Me | 69% at 40 |
| 20 | 4-OMe | 4-Cl | —CH(OH)Me | 19% at 40 |
| 21 | 4-Cl | 4-H | —CH$_2$OH | 52% at 50 |
| 22 | 2-OMe | 4-Cl | —CH$_2$OH | 33% at 50 |
| 23 | 4-OMe | 4-Cl | —COCH$_3$ | 53% at 40 |
| 24 | 4-OMe | 4-Cl | —CH$_2$OMe | 64% at 25 |
| 25 | 4-OMe | 4-Cl | —CH=CH—C$_6$H$_4$—CO$_2$Me | 18% at 25 |
| 26 | 4-OMe | 4-Cl | —CH=NOH | 79% at 25 |
| 28 | 4-OMe | 4-Cl | —CONEt$_2$ | 44% at 25 |
| 29 | 4-OMe | 4-Cl | —CONHOH | 91% at 25 |
| 30 | 4-OMe | 4-F | —CH$_2$OH | 42% at 25 |
| 31 | 4-OMe | 4-Cl | —CONH$_2$ | 75% at 25 |
| 32 | 4-OMe | 4-Cl | —CH=CH—(CH$_2$)$_3$—CO$_2$Na | 69% at 25 |
| 34 | 4-OMe | 4-Cl | —CONH—C$_6$H$_4$—OH | 21% at 25 |
| 35 | 4-Br | 4-Cl | —CH$_2$OH | 65% at 25 |
| 36 | 4-SO$_2$Me | 4-Cl | —CH$_2$OH | 40% at 50 |
| 37 | 4-CH$_3$ | 4-Cl | —CH$_2$OH | 41% at 25 |
| 38 | 4-OMe | 4-Cl | —CH=CH—(CH$_2$)$_3$—CONH$_2$ | 40% at 40 |
| 3a | 4-OMe | 4-Cl | —CON(CH$_3$)ONa | 65% at 10 |
| 44 | 4-OMe | 4-Cl | —CON(CH$_3$)OMe | 69% at 25 |
| 45 | 4-OMe | 4-F | —CON(CH$_3$)OH | 51% at 25 |
| 62 | 4-F | 4-Cl | —CH$_2$OH | 31% at 50 |
| 47 | 4-SMe | 4-Cl | —CH$_2$OH | 48% at 25 |
| 48 | 4-NO$_2$ | 4-Cl | —CH$_2$OH | 40% at 40 |

TABLE 16-continued

In Vivo Alleviation of Inflammation in Rats[1]

| No. | $R_1, R_2$[2] | $R_3, R_4$[3] | X | % INH. p.o.* (mpk) |
|---|---|---|---|---|
| 51 | 4-OC$_5$H$_{11}$ | 4-Cl | —CH$_2$OH | 6.4% at 30 |
| 53 | 4-OMe | 4-Cl | —CO$_2$NHMe | 94% at 40 |
| 54 | 4-OMe | 4-Ph | —CH$_2$OH | 36% at 25 |
| 55 | 4-OMe | 4-Me | —CH$_2$OH | [ED$_{50}$ = 3.9] |
| 56 | 4-OMe | 4-CF$_3$ | CH$_2$OH | [ED$_{50}$ = 3.0] |
| 57 | 4-OMe | 4-Cl | CO$_2$NH(tBu) | 87% at 25 |
| 58 | 4-OMe | 4-Cl | CON(tBu)OH | 47% at 25 |
| 59 | 4-OMe | 4-Cl | CH$_2$OCOCH$_2$COCH$_3$ | 48% at 20 |
| 60 | 2-CF$_3$ | 4-Cl | CH$_2$OH | 8% at 25 |
| 65 | 4-OMe | 4-Cl | CONHCH$_2$CH$_2$OH | 21% at 15 |
| 66 | 4-OMe | 4-Cl | CONHCH$_2$CO$_2$H | 62% at 25 |
| 67 | 4-H | 4-Cl | CON(CH$_3$)OH | 30% at 40 |
| 69 | 4-NH$_2$ | 4-Cl | CH$_2$OH | 17% at 15 |
| 72 | 4-OEt | 4-Cl | CO$_2$H | 71% at 15 |
| 74 | 3,4-diOMe | 4-Cl | CO$_2$H | 17% at 40 |
| 75 | 4-OEt | 4-Cl | CO$_2$Et | 73% at 40 |
| 76 | 4-OEt | 4-Cl | CON(CH$_3$)OH | 43% at 15 |
| 79 | 4-OMe | 4-CF$_3$ | CON(CH$_3$)OH | [ED$_{50}$ = 3.2] |
| 81 | 4-OMe | 4-Cl | CON(OH)iPr | 50% at 15 |
| 82 | 4-OMe | 4-Cl | CON(OH)cyclohexyl | 54% at 15 |
| 83 | 4-OMe | 4-Cl | CON(OH)Et | 42% at 15 |
| 84 | 4-OMe | 4-Cl | CON(OH)Ph | 27% at 40 |
| 85 | 4-OMe | 4-Cl | CONH-dihydrothiazoyl | 40% at 40 |
| 87 | 4-OMe | 4-Cl | COHNCH$_2$CO$_2$Et | 22% at 15 |
| 88 | 4-OMe | 4-Cl | CONHCH$_2$CONHOH | 36% at 15 |
| 89 | 4-OMe | 4-Cl | COHNCH$_2$CON(CH$_3$)OH | 57% at 15 |
| 90 | 4-OMe | 4-Cl | CONHtetrazole | 32% at 15 |
| 91 | 4-OMe | 4-Cl | CON(OBz)COCH$_3$ | 24% at 30 |
| 93 | 4-OMe | 4-Cl | CH$_2$OCH$_2$CO$_2$H | 17% at 15 |
| 96 | 4-OMe | 4-Cl | CH$_2$NH$_2$ | 56% at 30 |
| 100 | 4-OMe | 4-Cl | CONHCH(CO$_2$Et)CH$_2$SH | 58% at 15 |
| 101 | 4-OMe | 4-Cl | CONHCH(CO$_2$Et)CH$_2$SMe | 57% at 15 |
| 102 | 4-OMe | 4-Cl | CO$_2$NEt$_2$ | 87% at 30 |
| 103 | 2-OMe | 4-Cl | CO$_2$H | 55% at 10 |
| 105 | 4-OMe | 4-Me | CO$_2$H | 87% at 10 |
| 106 | 4-OMe' | 3-Me | CO$_2$H | 11% at 10 |
| 107 | 4-OMe | 3,4-di-Me | CO$_2$H | 30% at 10 |
| 109 | 4-OMe | 2-Me | CO$_2$H | 1% at 10 |
| 110 | 4-OMe | 4-Et | CO$_2$H | 51% at 10 |
| 104 | 2-OMe | 4-Cl | CON(CH$_3$)OH | 39% at 15 |
| 111 | 4-OMe | 4-Me | CON(CH$_3$)OH | 75% at 15 |
| 112 | 4-Cl | 4-OMe | CON(CH$_3$)OH | [ED$_{50}$ = 16.3] |
| 113 | 4-OMe | 4-OMe | CON(CH$_3$)OH | 34% at 10 |
| 114 | 4-OMe | 4-H | CON(CH$_3$)OH | 5% at 15 |
| 115 | 4-OMe | 3-Me | CON(CH$_3$)OH | 35% at 10 |
| 118 | 4-OMe | 2-Me | CON(CH$_3$)OH | 6% at 10 |
| 119 | 4-OMe | 4-Et | CON(CH$_3$)OH | 24% at 10 |
| 133 | 4-OMe | 4-Cl | CON(CH$_3$)OCOCH$_2$CH$_2$CO$_2$H | [ED$_{50}$ = 4.7] |
| 130 | 4-OMe | 4-Me | CON(CH$_3$)OCOCH$_2$CH$_2$CO$_2$H | [ED$_{50}$ = 11.5] |
| 132 | 4-OMe | 4-Cl | CON(CH$_3$)OCOCH$_2$CH$_2$CH$_2$CO$_2$H | 30% at 10 |
| 133 | 4-OMe | 4-Cl | CON(CH$_3$)OCOCH$_2$CH$_2$CO$_2$Na | 75% at 10 |
| 134 | 4-OMe | 4-Cl | CON(CH$_3$)OCOCH$_2$NMe$_2$ | [ED$_{50}$ = 12.5] |
| 135 | 4-OMe | 4-Cl | CON(CH$_3$)OCO-c-5H$_9$NHCO$_2$-t-Bu | 1% at 10 |
| 136 | 4-OMe | 4-Cl | CON(CH$_3$)OCOCH$_2$CH$_2$CO-Morpholine | 38% at 10 |
| 137 | 4-OMe | 4-Cl | CON(CH$_3$)OCOCH$_2$CH$_2$CONEt$_2$ | 54% at 10 |
| 138 | 4-OMe | 4-Cl | CON(CH$_3$)OCOCH$_2$NMe$_2$ | 17% at 10 |
| 139 | 4-OMe | 4-Cl | CON(CH$_3$)OCOCH$_2$Cl | [ED$_{50}$ = 6.0] |
| 140 | 4-OMe | 4-Cl | CON(CH$_3$)OCOCH$_3$ | 77% at 15 |
| 141 | 4-OMe | 4-Cl | CON(CH$_3$)OCOC(CH$_3$)$_3$ | 17% at 10 |
| 142 | 4-OMe | 4-Cl | CON(CH$_3$)OCOCH$_2$OMe | 67% at 10 |
| 143 | 4-OMe | 4-Cl | CON(OH)Pyr | 62% at 15 |
| 144 | 4-OMe | 4-Cl | CON(OH)CHMeCO$_2$Et | 55% at 10 |
| 145 | 4-OMe | 4-Cl | CON(OH)CHMeCo$_2$H | 61% at 10 |
| 146 | 4-OMe | 4-Cl | CON(OH)C$_8$H$_{17}$ | 29% at 10 |
| 151 | 4-OMe | 4-Cl | CH$_2$NHOH | 42% at 25 |
| 152 | 4-OMe | 4-Cl | CH$_2$N(OH)COCH$_3$ | 40% at 10 |
| 153 | 4-OMe | 4-Cl | CH$_2$N(OH)CO-t-Bu | 49% at 10 |
| 154 | 4-OMe | 4-Cl | CH$_2$N(OH)COC$_7$H$_{15}$ | 11% at 10 |
| 155 | 4-OMe | 4-Cl | CH$_2$N(OH)COPh | 45% at 10 |
| 156 | 4-OMe | 4-Cl | CH$_2$N(OH)SO$_2$CH$_3$ | 34% at 9 |
| 157 | 4-OMe | 4-Cl | CH$_2$N(OH)COCO$_2$Et | 51% at 10 |
| 158 | 4-OMe | 4-Cl | CH$_2$N(OH)COCONHOH | [ED$_{50}$ = 33.4] |
| 160 | 4-OMe | 4-Cl | NHCOCO$_2$Et | 9% at 15 |
| 163 | 4-OMe | 4-Cl | NHCOCON(Me)OH | 28% at 15 |
| 164 | 4-OMe | 4-Cl | CH$_2$NHCOCONHOH | 13% at 15 |
| 165 | 4-OMe | 4-Cl | NHCOCONHOH | 41% at 15 |
| 171 | 4-OMe | 4-Cl | CON(OH)COCH$_3$ | 62% at 10 |
| 172 | 4-OMe | 4-Cl | CON(OAc)COCH$_3$ | 83% at 15 |
| 173 | 4-OMe | 4-Cl | C(Me)=NNH-2-Thiazoline | 39% at 15 |
| 174 | 4-OMe | 4-Cl | CH=NNH-2-Thiazoline | 37% at 15 |

TABLE 16-continued

In Vivo Alleviation of Inflammation in Rats[1]

| No. | $R_1$, $R_2$[2] | $R_3$, $R_4$[3] | X | % INH. p.o.* (mpk) |
|---|---|---|---|---|
| 175 | 4-OMe | 4-Cl | C(Et)=NNH-2-Thiazoline | 16% at 10 |
| 176 | 4-OMe | 4-Cl | C(Ph)=NNH-2-Thiazoline | 6% at 15 |
| 177 | 4-OMe | 4-Cl | CH(OH)Et | 16% at 15 |
| 178 | 4-OMe | 4-Cl | CH(OH)Ph | 8% at 15 |
| 179 | 4-OMe | 4-Cl | CH(OH)-t-Bu | 36% at 10 |
| 180 | 4-OMe | 4-Cl | COEt | 32% at 15 |
| 181 | 4-OMe | 4-Cl | COPh | 30% at 15 |
| 185 | 4-OMe | 4-Cl | C(=NH)N(OH)Me | 5% at 15 |
| 186 | 4-OMe | 4-Cl | CONHC$_8$H$_{17}$ | 37% at 10 |

*% INH. p.o. = Percentage inhibition of pad swelling from per oral dosages in the amount of substituted pyrazole compound shown, where "mpk" is milligrams per kilogram of rat bodyweight and "ED$_{50}$" is the effective dose to obtain a 50% inhibition of inflammation.
[1] Abbreviations for substituents are as utilized in previous Tables and reaction Schemes. Additionally tBu is tert-butyl and Ph is phenyl.
[2] $R_2$ = hydrogen unless otherwise shown.
[3] $R_4$ = hydrogen unless otherwise shown.

In addition, the results for compounds of the structure shown below are shown in Table 17.

TABLE 17

| No. | R3,R4 | Y | X | % INH. p.o.* (mpk) |
|---|---|---|---|---|
| 147 | 4-Cl | Br | CO$_2$H | 79% at 15 |
| 182 | 4-Cl | Cl | CO$_2$H | 71% at 15 |
| 148 | 4-Cl | Br | CON(CH$_3$)OH | 15% at 40 |
| 149 | 4-Cl | Cl | CON(CH$_3$)OH | 68% at 15 |
| 150 | 4-Cl | Br | CONHOH | 70% at 15 |

The present invention has been described with respect to preferred embodiments. It will be clear to those skilled in the art that modifications and/or variations of the disclosed subject matter can be made without departing from the scope of the invention set forth herein.

Immune Complex-Induced Synovitis in the Dog Knee Joint

Mongrel dogs of either sex were anesthetized with 35 mg/kg pentobarbital i.v. A large bore needle attached to a syringe was inserted into the synovial space either through or just to the side of the patellar tendon. The accuracy of the puncture was assured by the aspiration of clear, viscous synovial fluid (time 0 sample). The syringe was removed and immune complexes (see below) were injected into the synovial space. The synovial space was re-entered at various time intervals and synovial fluid was withdrawn. The volume of fluid was recorded and then added to 3.0 ml of 0.3% saline. A sample was removed and the number of cells present counted with the use of a hemocytometer and microscope to enumerate the total number of cells in the joint. The remaining sample was centrifuged at 1000×g for 10 minutes and the supernatant analyzed for prostaglandin E$_2$ levels and leukotriene B$_4$ levels.

To prepare the immune complex, two hundred milligrams of partially purified dog IgG was dissolved in 20 ml 0.9% sterile sodium chloride. The solution was clarified by centrifugation at 2230×G at 20° C. for 10 minutes. A 3 ml volume of the 10.0 mg/ml solution of dog IgG was mixed with 1 ml rabbit anti-dog IgG serum and incubated at room temperature for 20 minutes.

Four milliliters of saturated ammonium sulfate were added to the mixture to precipitate the complex and all free dog IgG and rabbit gamma globulin. The sample was then centrifuged (as above) and the pellet resuspended in 10 ml 0.9% sterile saline. One ml of this solution was injected into a knee joint.

Following the intra-articular administration of immune complexes synovial fluid samples were taken at 30 minutes, 1,2,4 and 24 hours, alternating knees for sampling (except at 24 hours when both knees were sampled). Early in the course of events there is a rise in LTB$_4$ levels which peaks at 2 hours at approximately 8 ng/ml (FIG. 1). This early rise in leukotrienes is followed by an influx of cells into the synovial space and an increase in the prostaglandin levels which reach their peak at 4 hours. Theoretically, the elevated LTB$_4$ levels act as chemotactic factors for cell influx which then leads to prostaglandin production.

3-[5-(4-chlorophenyl)1-(4-methoxyphenyl)-3-pyrazolyl]-N-hydroxy-N-methylpropanamide (compound 3) was evaluated against a standard NSAID, naproxen, for its ability to inhibit immune complex-induced synovitis in the dog knee joint. Mongrel dogs were anesthetized with sodium pentobarbital (35 mg/kg i.v). The articular joint was entered and a zero time synovial fluid sample was removed. 1 ml of immune complexes was injected into the synovial joint of both legs. Vehicle or test compound was immediately injected intravenously (25 mg/kg) or administered orally at the doses shown in Tables 1, 2 and 3. Synovial fluid samples were taken at 30 minutes, 1, 2 and 4 hours. All samples were analyzed for total granulocyte count using a laser flow cytometer. Prostaglandin and leukotriene concentrations were determined with standard RIA techniques. Compound 3 significantly inhibits LTB$_4$ and PGE$_2$ levels as well as the total cell number present in the synovial fluid withdrawn from knee joints which have been injected intraarticularly with soluble immune complexes. Naproxen, at the same dose, inhibits PGE$_2$ levels and cellular infiltration, but does not decrease LTB$_4$ levels. These results confirm the dual inhibitory profile of compound 3.

As indicated from the above, compound 3 inhibits both the cyclooxygenase (CO) and 5-lipoxygenase (5-LO) enzymes which metabolize arachidonic acid (AA) into prostaglandins (PGs) and leukotrienes (LTs), respectively. This dual activity distinguishes the compounds of this invention from the non-steroidal antiinflammatory drugs (NSAIDs, e.g., naproxen, indomethacin) which only inhibit the cyclooxygenase enzyme. Compound 3 is an effective inhibitor of leukotriene production when administered orally to guinea pigs or dogs. Intravenous administration of 10 mg/kg AA to anesthetized guinea pigs pretreated with indomethacin (10 mg/kg) and propranolol (0.1 mg/kg) results in a sustained bronchospasm which is associated with increased blood levels of $LTB_4$. CO inhibitors (indomethacin) have no effect on this bronchospasm or $LTB_4$ levels while the compounds of this invention are effective inhibitors when administered orally ($ED_{50}=20$ to 160 mg/kg) or intravenously ($ED_{50}=15$ mg/kg). In the dog, intraarticular injection of rabbit anti-dog-dog IgG immune complexes into the knee joint results in an acute synovitis characterized by an influx of inflammatory cells into the joint space as well as an increase in synovial fluid levels of $PGE_2$ and $LTB_4$. When administered orally at 100 mg/kg, compound 3 reduces the cellular infiltrate and the levels of both $PGE_2$ and $LTB_4$ in the synovial fluid, while the NSAID, naproxen, (100 mg/kg) only inhibited the cell infiltration and the increase in $PGE_2$ levels but increased the $LTB_4$ levels (Tables 1, 2 and 3). These data clearly distinguish the compounds of this invention from the NSAIDs, and demonstrate their utility as antirheumatic drugs capable of inhibiting the production of $LTB_4$, which is associated with progressive chronic inflammatory disease such as rheumatoid arthritis.

An unexpected finding which further distinguishes compound 3 from NSAIDs is its lack of ulcerogenicity in the gastrointestinal tract. All NSAIDs are inhibitors of CO and their potency against this enzyme activity correlates well with clinical doses used in rheumatic diseases. There is also a correlation between CO inhibition (decreased $PGE_2$) and the ability to induce gastric lesions in the fasted rat model. All NSAIDs induce at least some gastrointestinal lesions within their therapeutic range. Naproxen, for example, causes significant ulcers in rats at suboptimal antiinflammatory doses. Compound 3 exhibits reduced ulcerogenic activity in rats at maximal antiinflammatory doses. The dose of compound 3 which induces ulcers in 50 percent of the rats ($UD_{50}$) is 173 mg/kg or 58 times the dose which inhibits the inflammatory response of the adjuvant rat by 50 percent ($ED_{50}=3$ mg/kg). A therapeutic ratio of 58 for compound 3 was determined in the following way:

thereapeutic ratio = Dose inducing ulcers in 50% of animals = $UD_{50}$, divided by Dose reducing inflammatory response by 50% = $ED_{50}$ In dogs, Compound 3 exhibited no significant gastrointestinal side effects at doses up to 2700 mg/kg after administration for one week.

TABLE 1

Immune Complex Induced Synovitis in the Dog Knee Joint

| Treatment | N | Cellular Infiltrate Total Cells ($\times 10^6$) | | | |
|---|---|---|---|---|---|
| | | 0.5 HR | 1 HR | 2 HR | 4 HR |
| Methocel Control p.o. | 9 | 0.2 ± 0.29 | 0.64 ± 0.36 | 6.2 ± 2.1 | 49.5 ± 13.4 |
| Compound 3 25 mg/ kg, p.o. | 5 | 0.12 ± 0.04 | 0.39 ± 0.19 | 5.74 ± 2.5 (7.4% I) | 46.3 ± 27.9 (6.5% I) |
| Compound 3 100 mg/ kg, p.o. | 5 | 0.26 ± 0.23 | 0.13 ± 0.07 | 1.35 ± 0.55 (78% I) | 22.2 ± 6.6 (55.2% I) |
| Naproxen | 4 | 0.32 ± 0.11 | 0.02 ± 0.02 | 2.69 ± 0.63 (36.6% I) | 27.6 ± 24 (44.2% I) |

I = Inhibition

TABLE 2

Immune Complex-Induced Synovitis in the Dog Knee Joint

| Treatment | N | *Prostaglandin $E_2$ Levels (mg/ml synovial fluid) | | | |
|---|---|---|---|---|---|
| | | 0.5 Hr | 1 Hr | 2 Hr | 4 Hr |
| Methocel Control | 9 | 1.80 ± 0.84 | 1.07 ± 0.27 | 4.79 ± 3.10 | 4.10 ± 0.94 |
| Compound 3 25 mg/ kg p.o. | 5 | | 2.34 ± 1.0 | 2.96 ± 0.92 (38.2% I) | 2.27 ± 0.76 (44.6% I) |
| Compound 3 100 mg/ kg, p.o. | 5 | 1.80 ± 1.29 | 1.50 ± 1.05 | 0.10 ± 0.08 (97.9% I) | 2.36 ± 0.53 (42.4% I) |
| Naproxen 100 mg/ kg, p.o. | 4 | 0.83 ± 0.24 | 1.67 ± 0.73 | 1.88 ± 0.86 (62.0% I) | 2.20 ± 0.97 (44.9% I) |

*Measured by radioimmunoassay

TABLE 3

Immune Complex-Induced Synovitis in the Dog Knee Joint

| Treatment | N | Leukotriene $B_4$ ng/ml Synovial Fluid | | | |
|---|---|---|---|---|---|
| | | 0.5 Hr | 1 Hr | 2 Hr | 4 Hr |
| Methocel Control | 9 | 1.24 ± 0.22 | 2.58 ± 0.51 | 4.03 ± 0.86 | 1.40 ± 0.33 |
| Compound 3 25 mg/ kg p.o. | 5 | | 3.00 ± 1.2 | 4.60 ± 2.10 | 1.20 ± 0.6 |
| Compound 3 100 mg/ kg, p.o. | 5 | 0.93 ± 0.26 (25% I) | 0.80 ± 0.09 (69% I) | 2.46 ± 0.94 (39% I) | 0.88 ± 0.23 (37% I) |
| Naproxen 100 mg/ kg, p.o. | 4 | 1.11 ± 0.36 (10.5% I) | 3.27 ± 1.53 (−26.7% I) | 5.94 ± 1.33 (−47.4% I) | 3.36 ± 1.28 (−140% I) |

What is claimed is:

1. A method for treating rheumatoid arthritis in a mammal which comprises administering to said mammal an effective amount of a compound of the formula:

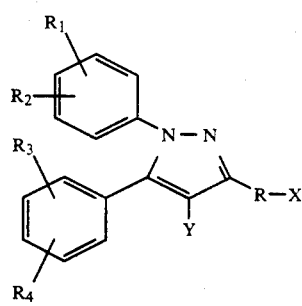

wherein
- R₁, R₂, R₃ and R₄ are the same or different and are individually selected from the group consisting of hydrogen, lower alkyl, lower alkoxy, phenyl, halo, hydroxy, lower alkylsulfonyl, lower alkylthio, nitro, trifluoromethyl, omega-trifluoromethyl lower alkoxy, amino, acetamido, carboxy, alkylhydroxamic acid, or where R₁R₂ or R₃R₄, taken together with the phenyl group to which they are attached, form a naphthyl or substituted naphthyl group;
- R is a straight chained, saturated hydrocarbon that contains 2–16 carbon atoms:
- Y is hydrogen, bromo, chloro or lower alkyl;
- and X is selected from the group consisting of carboxy, hydroxy, alkanoyloxy, lower alkoxy, lower alkyl carbonyl, oximino, cyano, amino, —C(O)—R₅, —C(O)C(O)—R₅, —NR₈OH, —NHR₁₃, —C(R₁₄)=NNH-thiazolino —CH(OH)R₁₄, —C(=NH)N(OH)-lower alkyl;
- wherein R₅ is selected from the group consisting of hydrogen, alkyl, lower alkoxy, NR₆R₇ and —O—NR₁₅R₁₆;
- wherein R₆ is R₇ are the same or different and are selected from the group consisting of hydrogen, lower alkyl, lower alkoxy, hydroxy, acyloxy, benzyloxy, 2-hydroxy lower alkyl, carboxy lower alkyl, phenyl, pyridyl, thiazolyl, dihydrothiazolyl, 5-tetrazolyl, —OCO(CH₂)n COR₉ and —OCOR₁₀;
- wherein R₈ is hydrogen, —CO-loweralkyl, —CO-t-butyl, —COC₇H₁₅, CO-phenyl, SO₂-lower alkyl, —COCO₂-lower alkyl, or —COCONHOH;
- wherein R₉ is —OH, —ONa, or dialkylamino and n is 2 or 3;
- wherein R₁₀ is —CH₂NR₁₁R₁₂, —CH₂Cl, —CH₂O-loweralkyl, t-butyl, or —CH-loweralkyl-CO₂ Q, wherein Q is lower alkyl or H;
- wherein R₁₁ and R₁₂ are the same or different and are any of alkyl, cyclohexyl, or together form N-methylpiperazino;
- wherein R₁₃ is hydrogen, —CO-lower alkyl, —CO-t-butyl, —COC₇H₁₅, —CO-phenyl, —SO₂-lower alkyl, —COCO₂-lower alkyl, —COCONHOH, —COCO₂H, COCON(lower alkyl)OH or PO(O-lower alkyl)₂;
- wherein R₁₄ is hydrogen, phenyl or t-butyl;
- wherein R₁₅ and R₁₆ are the same or different are selected from the group consisting of hydrogen, lower alkyl and phenyl;
- with the provisos that:
  (a) when Y is bromo or chloro, X is —COOH, —CH₂OH or —C(O)—R₅ wherein R₅ is NR₆R₇ and R₆ is OH and R₇ is lower alkyl;
  (b) at least one R₁ and R₂ is other than hydrogen where (i) R—X is (CH₂)₂CO₂H or (CH₂)₂C(O)N-HOH, and (ii) R₃ and R₄ are 4-methoxy, 3-methoxy-4-hydroxy, 2-hydroxy and hydrogen and
  (c) at least one of R₁ and R₂, or of R₃ and R₄ is other than hydrogen where R—X together contains three saturated carbon atoms linked together by carbon-carbon bonds; and pharmaceutically acceptable salts thereof.

2. The method of claim 1 wherein the compound is 3-[5-(4-chlorophenyl)-1-(4-methoxyphenyl)-3-pyrazolyl]-N-hydroxy-N-methylpropanamide.

3. The method of claim 1 wherein the compound is selected from the group consisting of 5-(4-chlorophenyl)-3-(3-hydroxypropyl)-1-(4-methoxyphenyl) pyrazole;
5-(4-trifluoromethylphenyl)-3-(3-hydroxypropyl)-1-(4-methoxyphenyl) pyrazole;
1-(4-bromophenyl)-5-(4-chlorophenyl)-3-(3-hydroxypropyl) pyrazole;
8-[5-(4-chlorophenyl)-1-(4-methoxyphenyl)-3-pyrazolyl]-5(Z)-octenoate;
3-[5-(4-chlorophenyl)-1-(4-methoxyphenyl)-3-pyrazolyl]propanoate;
3-[5-(4-chlorophenyl)-1-(4-methoxyphenyl)-3-pyrazolyl]-N-tert-butyl-N-hydroxypropanamide; and
N-carboxymethyl-3-[5-(4-chlorophenyl)-1-(4-methoxyphenyl)-3-pyrazolyl]-propanamide.

4. A method for treating rheumatoid arthritis in a mammal which comprises administering to said mammal an effective amount of a compound of the formula

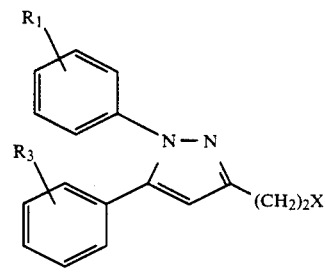

wherein
- R₁ and R₃ are selected from the group consisting of halo, trifluoromethyl, methyl, phenyl and methoxy; and
- X is selected from the group consisting of carboxy, C(O)—R₅ wherein R₅ is selected from the group consisting of N(CH₃)OH, N(t-C₄H₉)OH, NHOH, ONH(CH₃) and ONH(t-C₄H₉).

5. The method of claim 1, wherein the substituted naphthyl group is substituted by a substituent selected from the group consisting of halo, trifluoromethyl, lower alkyl and lower alkoxy.

6. The method of claim 1, wherein the substituted phenyl is substituted by a substituent selected from the group consisting of halo, trifluoromethyl, lower alkyl and lower alkoxy.

7. The method of claim 1, wherein R₁ is 4-methoxy, R₂ is H, R₃ is 4-Cl, R₄ is H, R is (CH₂)₂ and X is CON(OH)cyclohexyl.

8. A compound of the formula

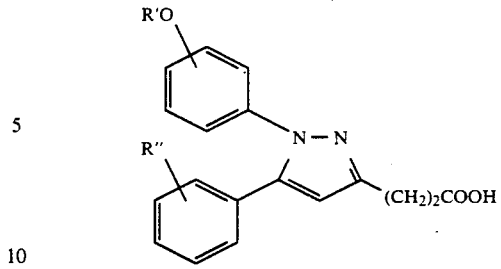
wherein R' is lower alkyl and R" is halo or lower alkyl.
9. The compound of claim 8 which compound is 3-[5-(4-chlorophenyl)-1-(4-methoxyphenyl)-3-pyrazolyl]propionic acid.
10. The compound of claim 8 which compound is 3-[5-(4-methylphenyl)-1-(4-methoxyphenyl)-3-pyrazolyl]propionic acid.
* * * * *